United States Patent
Veruva et al.

(10) Patent No.: US 12,168,081 B2
(45) Date of Patent: Dec. 17, 2024

(54) HIGHLY ELASTIC MEDICAL SEALANTS FOR FLEXIBLE SOFT TISSUE

(71) Applicant: Ethicon, Inc., Raritan, NJ (US)

(72) Inventors: Sai Veruva, Raritan, NJ (US); Salim Ghodbane, Raritan, NJ (US); Thomas Weindl, Somerville, NJ (US)

(73) Assignee: Ethicon, Inc., Raritan, NJ (US)

( * ) Notice: Subject to any disclaimer, the term of this patent is extended or adjusted under 35 U.S.C. 154(b) by 47 days.

(21) Appl. No.: 17/738,636

(22) Filed: May 6, 2022

(65) Prior Publication Data

US 2023/0355831 A1 Nov. 9, 2023

(51) Int. Cl.
*A61L 24/00* (2006.01)
*A61L 24/04* (2006.01)

(52) U.S. Cl.
CPC ....... *A61L 24/0042* (2013.01); *A61L 24/0026* (2013.01); *A61L 24/0031* (2013.01); *A61L 24/043* (2013.01); *A61L 24/046* (2013.01)

(58) Field of Classification Search
CPC ............ A61L 24/0042; A61L 24/0026; A61L 24/0031; A61L 24/043; A61L 24/046
See application file for complete search history.

(56) References Cited

U.S. PATENT DOCUMENTS

| | | |
|---|---|---|
| 8,034,367 B2 | 10/2011 | Hnojewyj |
| 9,040,074 B2 | 5/2015 | Holzer et al. |
| 9,295,752 B1 | 3/2016 | Girdhar |
| 10,039,709 B2 | 8/2018 | Alur et al. |
| 10,322,170 B2 | 6/2019 | Gulle et al. |
| 2006/0088570 A1 | 4/2006 | Cruise |
| 2016/0271228 A1 | 9/2016 | Gulle et al. |
| 2019/0269818 A1 | 9/2019 | Dhanaraj et al. |

OTHER PUBLICATIONS

Elvin et al. (Biomaterials 31(2010) 8323-8331).*
Varma et al. (Acta Biomaterialia; 10(12) 2014; 4996-5004).*
Chen et al. (International J. Pharmaceutics 288 (2005)207-2180.*
Al-Shamkhani, Aymen et al., "Radioiodination of Alginate via Covalently-Bound Tyrosinamide Allows Monitoring of its Fate In Vivo", In Journal of Bioactive and Compatible Polymers, vol. 10, pp. 4-13, Jan. 1995.
Alcázar-Alay, SC et al., "Physicochemical Properties, Modifications and Applications of Starches from Different Botanical Sources", In Food Science and Technology, vol. 35, pp. 215-236, Apr. 2015.
Asanza Teruel, ML et. al., "Response Surface Analysis of Chlortetracycline and Tetracycline Production with K-Carrageenan Immobilized Streptomyces Aureofaciens", In Enzyme and Microbial Technology, vol. 21, pp. 314-320, Oct. 1997.
Baghale et al., "Wound Healing Properties of PVA/Starch/Chitosan Hydrogel Membranes with Nano Zinc Oxide as Antibacterial Wound Dressing Material", in Journal of Biomaterials Science, Polymer edition, vol. 28, pp. 2220-2241, Oct. 2017.
Barth, et al., "A Review of Polymer Shear Degradation in Size-Exclusion Chromatography" Journal of Liquid Chromatography, vol. 7, pp. 1717-1738, Aug. 1984.
Bouhadir et al., "Degradation of Partially Oxidized Alginate and its Potential Application for Tissue Engineering" Biotechnology Progress, vol. 17, pp. 945-950, Sep. 2001.
Bursali et al., "Synthesis, Characterization and in Vitro Antimicrobial Activities of Boron/Starch/Polyvinyl Alcohol Hydrogels", In Carbohydrate Polymers, vol. 83, pp. 1377-1383, Jan. 2011.
Eccles et al., "Efficacy and Safety of Iota-Carrageenan Nasal Spray Versus Placebo in Early Treatment of the Common Cold in Adults: the ICICC Trial", In Respiratory Research, vol. 16, No. 121, 12 pages, Dec. 2015.
Elvira et al., "Starch-Based Biodegradable Hydrogels with Potential Biomedical Applications as Drug Delivery Systems", In Biomaterials, vol. 23, pp. 1955-1966, May 2002.
Fazekas et al., "Lessons Learned from a Double-blind Randomised Placebo-Controlled Study with a Iota-Carrageenan Nasal Spray as Medical Device in Children with Acute Symptoms of Common Cold", In BMC complementary and Alternative Medicine, vol. 12, No. 147, Dec. 2012.
Florek et al., "Results from a First in-Human Trial of a Novel Vascular Sealant", In Frontiers in Surgery, vol. 2, No. 29, Jul. 2015.
Gioffredi et al., "Pluronic F127 Hydrogel Characterization and Biofabrication in Cellularized Constructs for Tissue Engineering Applications", In Procedia CIRP, vol. 49, pp. 125-132, Jan. 2016.
Han et al., "Structural Changes in Corn Starches during Alkaline Dissolution by Vortexing", In Carbohydrate Polymers, vol. 55, pp. 193-199, Jan. 2004.
Heinze et al., "Carboxymethyl Ethers of Cellulose and Starch—A Review", Macromolecular Symposia, vol. 23, pp. 13-40, Mar. 2005.
Hernández et al., "Viscous Synergism in Carrageenans (κ and λ) and Locust Bean Gum Mixtures: Influence of Adding Sodium Carboxymethylcellulose", Food Science and Technology International, vol. 7, pp. 383-391, Oct. 2001.
Kamoun et al., "A Review on Polymeric Hydrogel Membranes for Wound Dressing Applications: PVA-based Hydrogel Dressings", In Journal of Advanced Research, vol. 8, pp. 217-233, May 2017.
Kirwan et al., "The Skin and Wound Healing", In Pathology and Intervention in Musculoskeletal Rehabilitation (Second Edition), Chapter 2, pp. 25-62, Dec. 2016.
Lee et al., "Alginate: Properties and Biomedical Applications", In Progress in Polymer Science, vol. 37, pp. 106-126, Jan. 2012.
Leveriza-Oh et al., "Dressings and Postoperative Care", Lower Extremity Soft Tissue & Cutaneous Plastic Surgery (Second Edition), Chapter 32, pp. 471-488, Jan. 2012.

(Continued)

*Primary Examiner* — Shirley V Gembeh
(74) *Attorney, Agent, or Firm* — David R. Crichton; Leo B. Kriksunov

(57) ABSTRACT

Provided herein are compositions, systems and surgical methods for treating expandable soft tissue utilizing a reactive liquid hydrogel sealant mixture including a cross-linkable electrophilic compound, a nucleophilic compound, and an amphiphilic poly(alkyl)ene glycol block polymer in an amount of 20% (w/v) or less of the sealant composition. The composition can optionally include a viscosifier, in an amount of 0.1% to 1.0% (w/v) of the sealant composition.

12 Claims, 12 Drawing Sheets

(56) References Cited

OTHER PUBLICATIONS

Martins et al., "Hierarchical Starch-Based Fibrous Scaffold for Bone Tissue Engineering Applications", Journal of Tissue Engineering and Regenerative Medicine, vol. 3, pp. 37-42, Jan. 2009.
Mir et al., "Synthetic Polymeric Biomaterials for Wound Healing: A Review", Progress in Biomaterials, pp. 1-21, Mar. 2018.
Nadagouda et al., "Synthesis of Thermally Stable Carboxymethyl Cellulose/Metal Biodegradable Nanocomposites for Potential Biological Applications", Biomacromolecules, vol. 8, pp. 2762-2767, Sep. 2007.
Necas et al., "Carrageenan: A review", In Veterinarni Medicina, vol. 58, No. 4, pp. 187-205, Apr. 2013.
Orive et al., "Biocompatibility of Microcapsules for Cell Immobilization Elaborated with Different Type of Alginates", In Biomaterials, vol. 23, pp. 3825-3831, Sep. 2002.
Pang, Suh Cem, et al, "Starch-Maleate Polyvinyl Alcohol Hydrogels with Controllable Swelling Behaviors", In Carbohydrate Polymers. vol. 84, pp. 424-429, Feb. 2011.
Reis et al., "Characterization of Two Biodegradable Polymers of Potential Application within the Biomaterials Field", In Journal of Materials Science: Materials in Medicine, vol. 6, pp. 786-792, Dec. 1995.
Sannino et al., "Biodegradable Cellulose-based Hydrogels: Design and Applications", In Materials, vol. 2, pp. 353-373, Apr. 2009.
Sarker et al., "Rheological Behavior of Starch-Based Biopolymer Mixtures in Selected Processed Foods", Starch-Stärke, vol. 65, pp. 73-81, Jan. 2013.
Shi et al., "Effects of Food Gums on Viscosities of Starch Suspensions during Pasting", In Carbohydrate Polymers, vol. 50, pp. 7-18, Oct. 2002.
Stoeber, et al., "Flow Control in Biomedical Microdevices using Thermally Responsive Fluids", In books of Biomaterials for MEMS, Mar. 2011.
Takamatsu, et al., "Production of L-alanine and D-aspartic acid", In Bioprocess Technology, pp. 25-35, 1993.
Therkelsen GH, "In Industrial Gums (Third Edition)", Chapter 7, pp. 145-180, Jan. 1993.
Torres et al., "Biodegradability and Mechanical Properties of Starch Films from Andean Crops", In International Journal of Biological Macromolecules, vol. 48, pp. 603-606, May 2011.
Torres et al., "Starch-Based Biomaterials for Wound-Dressing Applications", Starch-Stärke, vol. 65, pp. 543-551, Jul. 2013.
Velde et al., "Carrageenan: A Food-Grade and Biocompatible Support for Immobilisation Techniques", Advanced Synthesis Catalysis, vol. 344, pp. 815-835, Sep. 2002.
Wilson, "Foams: Physics, Chemistry and Structure", Springer Series in Applied Biology, pp. 1-15, 1989.
Wang et al., "Controlling the Moisture Absorption Capacity in a Fiber-Reinforced Thermoplastic Starch using Sodium Trimetaphosphate", In Industrial Crops and Products, vol. 36, pp. 299-303, Mar. 2012.
Zacharopoulos et al., "Vaginal Formulations of Carrageenan Protect Mice from Herpes Simplex Virus Infection", In Clinical and diagnostic laboratory immunology, vol. 4, pp. 465-468, Jul. 1997.
"Safety Evaluation of Certain Food Additives", In Seventy-ninth meeting of the Joint FAO/WHO Expert Committee on Food Additives Geneva, 378 pages, Jul. 2015.
International Search Report dated Aug. 2, 2023 for International Appln. No. PCT/IB2023/054570.

\* cited by examiner

HIGHLY ELASTIC MEDICAL SEALANTS FOR FLEXIBLE SOFT TISSUE

FIELD OF DISCLOSURE

The present disclosure describes liquid compositions for forming crosslinked-bioabsorbable elastic sealants that are suitable to use in the repair of expandable soft tissue.

BACKGROUND

Cross-linkable mixtures of synthetic polymers and/or biologics are widely used as surgical sealants. These products typically start as separate liquid components that upon application will react with one another and form a strong-crosslinked gel. The design of surgical sealants often involves considerations of usability of the delivery device and the mechanical properties of the sealant mechanics. In regard to usability, the viscosity of the sealant is essential to allow for a targeted application of the sealant. The efficacy of the sealant is directly a result of the mechanics of the resultant gel, including tensile properties, adhesive properties, and burst pressure. For example, when used as a pleural sealant, elasticity is important for maintaining a durable and flexible seal during pulmonary expansion and contraction cycles. There are several disadvantages with current commercial synthetic sealants. For example, Progel™, an FDA-approved liquid sealant indicated for sealing pleural air leaks, suffers from low viscosity, leading to difficulty retaining the solution at the desired site of application, as well as insufficient ability to stretch, leading to delamination from the plural surface during cyclic pulmonary expansion.

One solution to low viscosity is to incorporate rheological modifiers, such as polysaccharides and natural gums, to increase the viscosity of the liquid sealant and thereby reduce run-off of the liquid phase. Typically, viscosity agents are chosen in a manner so that they do not react with the active components of the sealant. As a result, these agents provide no additional benefit to the elasticity or cohesiveness of the resultant gel and, in some cases, results in a reduction in elasticity, possibly due to an adverse effect on mixing.

Thus, there is a need to provide sealants for soft tissues that meet the clinical needs for elasticity and strength, have improved handling properties, including viscosity, and can withstand cyclic expansion and contraction.

SUMMARY

The present disclosure is directed to compositions suitable for use as a soft-tissue sealant, and in particular, for use as a pleural sealant. In order to function as a clinically effective tissue sealant, sealant compositions must have a sufficiently high viscosity prior to curing in order to inhibit flow from the anatomical site of application, as well as exhibiting a sufficiently high tensile strength and elongation after curing in order to maintain an appropriate seal and prevent delamination of the sealant from the anatomical site.

Accordingly, the present disclosure describes liquid compositions for forming a crosslinked sealant that are suitable to use in the repair of expandable soft tissue. The liquid compositions according to the present disclosure are reactive hydrogel mixtures of an electrophilic compound and nucleophilic compound that are cross-linkable with each other via reaction of the available electrophilic and nucleophilic moieties of each compound; an amphiphilic poly(alkyl)ene glycol block polymer, and, a buffer solution having a pH in the range of about 8.5 to about 10.5. The electrophilic compound can include a multi-arm polyethylene glycol (PEG) based polymer, and the nucleophilic compound can include a multi-arm polymer containing at least one reactive amine group, or thiol group. Preferably, the liquid compositions include a buffer solution having a pH in the range of about 8.5 to about 9.0.

The present disclosure describes improvements to biocompatible sealants demonstrating that adding an amphiphilic poly(alkyl)ene glycol block polymer, in modest amounts (<20% w/v) produced unexpected benefits of increased viscosity of liquid phase co-mixture and improved elasticity of the resultant hydrogel. The present disclosure describes further improvements to the above-mentioned sealants with the addition of a viscosifier, such that an unexpected and synergistic effect of the amphiphilic poly (alkyl)ene glycol block polymer and the viscosifier produces improved viscosity, elasticity, adhesive, and cohesive properties, as compared to the conventionally known biocompatible sealants. In addition to improved sealant tensile properties, the addition of the amphiphilic poly(alkyl)ene glycol block polymer can provide benefits in the potential for drug delivery. Amphiphilic poly(alkyl)ene glycol block polymer have capabilities in encapsulating and delivering hydrophobic drugs, and those capabilities may be leveraged in liquid compositions described herein to provide therapeutic benefit to a target anatomical site of application.

In certain embodiments, the amphiphilic poly(alkyl)ene glycol block polymer is present in the liquid compositions in an amount of about 20% (w/v) or less of the liquid composition, such as, for example, in the range of about 5% to about 15% (w/v), or about 7.5% to about 12.5% (w/v). In further embodiments, the amphiphilic poly(alkyl)ene glycol block polymer includes base units of polyethylene glycol, polypropylene glycol, and copolymers thereof, such as, for example, a triblock copolymer including a central block of polypropylene glycol and two end blocks of polyethylene glycol (PEG).

In additional embodiments the liquid composition further includes a viscosifier, or a mixture of at least two different viscosifier. In certain embodiments the viscosifier includes at least carboxymethyl cellulose (CMC) or carrageenan. In certain further embodiments, the viscosifier is present in the liquid composition in an amount in the range of about 0.1% to about 10% (w/v).

In certain embodiments, the electrophilic compound includes at least one of 4-arm PEG-N-hydroxysuccinimide (PEG-NHS), or more specifically 4-arm PEG-succinimidyl glutarate ester (PEG-SG). In certain additional embodiments, the nucleophilic component includes at least one of 4-arm PEG-amine or albumin.

The present disclosure further describes systems for forming crosslinking sealants for use in the repair and treatment of soft tissues. According to certain embodiments, the systems can include a first container containing a first liquid and a second container containing a second liquid, where the first liquid has a buffer solution having a pH in the range of about 8.5 to about 9.0, a cross-linkable electrophilic compound, and an amphiphilic poly(alkyl)ene glycol block polymer; and, the second liquid has a buffer solution having a pH in the range of about 8.5 to about 9.0, and a cross-linkable nucleophilic compound, wherein the electrophilic and nucleophilic compounds are cross-linkable with each other via reaction of the available electrophilic and nucleophilic moieties of each compound. In the disclosed systems, the cross-linkable electrophilic compound and the cross-linkable nucleophilic compound are configured to form a crosslinked soft tissue sealant upon admixture of the first liquid and the second liquid. According to further embodiments, the first container can further include a viscosifier, as described above.

The present disclosure additionally describes a surgical method of treating or repairing soft tissue, for example, pleural tissue that includes the steps of:

mixing a first liquid contained in a first container and a second liquid contained in a second container to form a liquid soft tissue sealant, where the first liquid includes a buffer solution having a pH in the range of about 8.5 to about 9.0, a cross-linkable electrophilic compound, and an amphiphilic poly(alkyl)ene glycol block polymer; and the second liquid includes a buffer solution having a pH in the range of about 8.5 to about 9.0, and a cross-linkable nucleophilic compound;

forming a liquid cross-linked tissue sealant from the mixture of the first and second fluids; and, applying the liquid cross-linked tissue sealant to a pleural tissue to cover a target surface

DETAILED DESCRIPTION

Figure 1A:
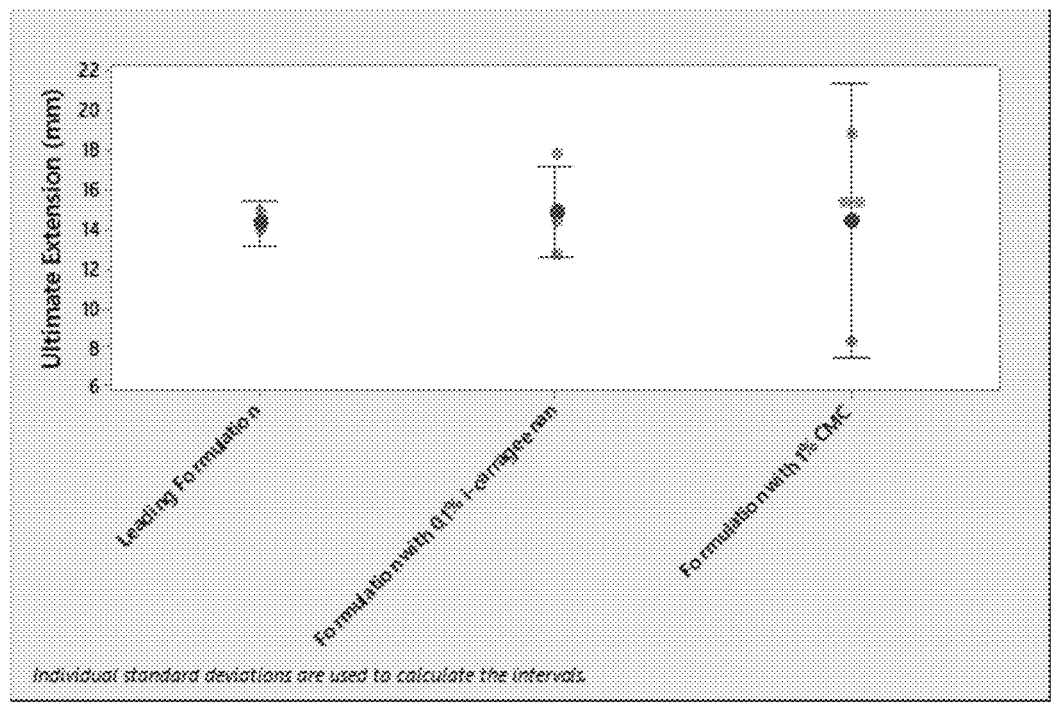
FIG. 1A is a graphical representation of ultimate extension of a control sample, and two different samples of the control with a viscosifier added.
Figure 1B:
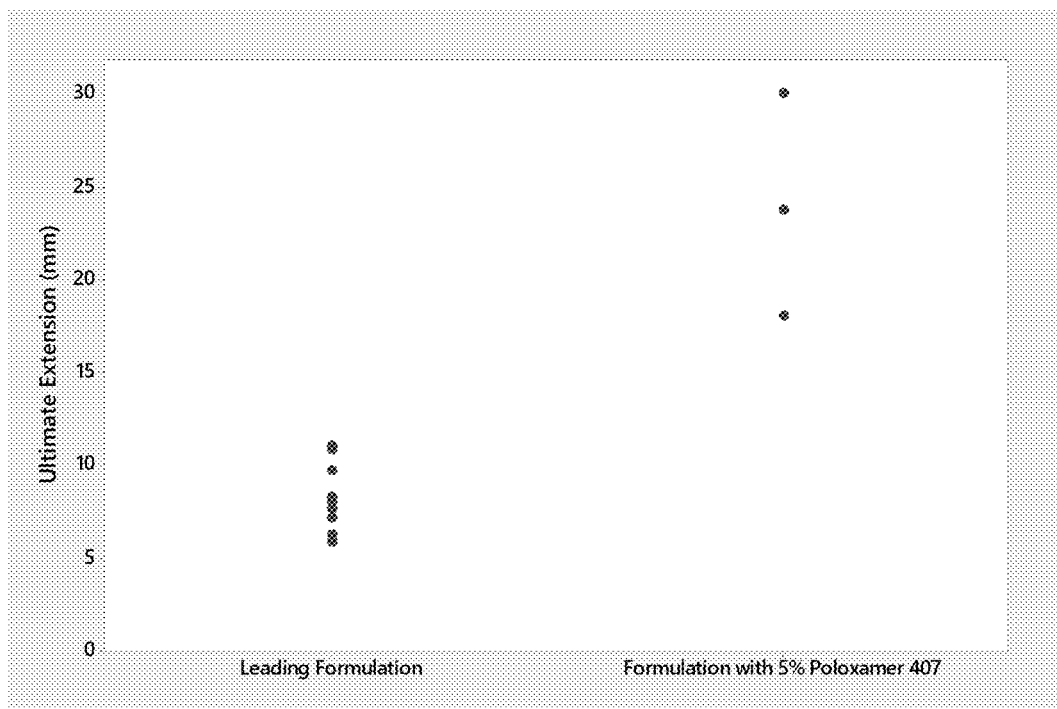
FIG. 1B is a graphical representation of ultimate extension of the control sample of FIG. 1A, and a formulation according to the present disclosure including the amphiphilic poly(alkyl)ene glycol block polymer (Poloxamer 407)

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable. Further, reference to values stated in ranges includes each and every value within that range. It is also to be appreciated that certain features of the invention, which, for clarity, are described herein in the context of separate embodiments, may also be provided in combination in a single embodiment. Conversely, various features of the invention that are, for brevity, described in the context of a single embodiment, may also be provided separately or in any subcombination.

As used herein the phrase "consisting essentially of" is intended to define the scope of a claim as including the recited components, compounds, substances, materials, or steps, and additionally include any components, compounds, substances, materials, or steps that do not materially affect the basic characteristics of the claimed invention.

The present disclosure describes liquid compositions for forming a crosslinked sealant that are suitable to use in the repair of expandable soft tissue. Preferably, the soft tissue is pleural tissue. The liquid compositions according to the present disclosure are reactive hydrogel mixtures of an electrophilic compound and nucleophilic compound that are cross-linkable with each other via reaction of the available electrophilic and nucleophilic moieties of each compound; an amphiphilic poly(alkyl)ene glycol block polymer; and, a buffer solution having a pH in the range of about 8.5 to about 9.0.

The electrophilic and nucleophilic reactive compounds that form the cross-linked structure of the hydrogel sealant are known in the art, and can include both synthetic polymers, such as multi-arm polyethylene glycol (PEG) based polymers, and natural substances, as well as combinations thereof. Multi-arm PEGs suitable for the elastic layer can include 2, 3, 4, 6 or 8 multi-arm PEGs. In preferred embodiments, the multi-arm PEG has a molecular weight of about 2 kDa to about 40 kDa.

According to certain embodiments, synthetic polymer can include polymers having activated esters, such as from the class of compounds of PEG-N-hydroxysuccinimide (PEG-NHS), PEG-aldehydes, PEG-acrylates, Carboxyl-PEGs, and 4-arm vinyl-PEGs. According to further embodiments, a non-exhaustive list of suitable electrophilic compounds can include 4-arm-PEG-succinimidyl glutarate (SG), 4-arm-PEG-succinimidyl valerate, 4-arm-PEG-succinimidyl carbonate, 4-arm-PEG-succinimidyl succinate, 4-arm-PEG-succinimidyl butanoate, 4-arm-PEG-succinimidyl succinamide, 4-arm-PEG-succinimidyl propionate, 4-arm-PEG-sulfosuccinimidylglutarate (SG), 4-arm-PEG-sulfosuccinimidylvalerate, 4-arm-PEG-sulfosuccinimidylcarbonate, 4-arm-PEG-sulfosuccinimidylsuccinate, 4-arm-PEG-sulfosuccinimidylbutanoate, 4-arm-PEG-sulfosuccinimidylsuccinamide, 4-arm-PEGsulfosuccinimidylpropionate, and 4-arm-PEG-isocyanate, 4-arm-PEG-imidoester, 4-arm-PEG-maleimide, 4-arm-PEG-acetic acid, 4-arm-PEG-propanoic acid, 4-arm-PEG-butanoic acid, 4-arm-PEG-hexanoic acid, and 4arm-PEG-vinylsulfone. Other examples include 2 arm, 3 arm, 6 arm, and 8 arm-PEGs of the exemplary 4-arm compounds listed above. As previously described, the electrophilic compound can include a blend of natural and synthetic components.

In certain embodiments, the nucleophilic compounds include natural compounds, such as albumin, gelatin, or collagen. In certain additional embodiments, the nucleophilic compounds can include a synthetic polymer, preferably a multi-arm polymer. In further embodiments, the nucleophilic compound contains at least one reactive amine group, such as, for example, a 4-arm PEG-amine or PEG-hydrazide, or 4-arm PEG-thiol.

Amphiphilic poly(alkyl)ene glycol block polymers suitable according to the present disclosure include compounds from the class of polyether polyols, such as, for example, polyethylene glycol (PEG) and polypropylene glycol (PPG), as well as copolymers and mixtures thereof. In preferred embodiments, the block polymer is a co-block polymer or a tri-block polymer, containing both PEG and PPG units. For example, one suitable class of compounds is commonly known as poloxamers, and includes triblock copolymers composed of a central hydrophobic chain of PPGs flanked by two hydrophilic chains of PEGs triblock copolymer consisting of a central hydrophobic block of polypropylene glycol flanked by two hydrophilic blocks of polyethylene glycol (PEG). Poloxamers are also commonly known by the trade name Pluronic. A particularly preferred embodiment is Poloxamer 407 (also known as Pluronic F127).

According to the present disclosure, the amphiphilic poly(alkyl)ene glycol block polymer is present in an amount of 20% (w/v) or less of the sealant composition; preferably, in a range of about 5% to about 15% (w/v); and, particularly preferred in a range of about 7.5% to about 12.5% (w/v) of the sealant composition.

In certain embodiments, the liquid compositions according to the present disclosure consist essentially of reactive hydrogel mixtures of a cross-linkable electrophilic compound and nucleophilic compound; an amphiphilic poly(alkyl)ene glycol block polymer, and, a buffer solution having a pH in the range of about 8.5 to about 9.0. In preferred embodiments, the liquid compositions according to the present disclosure consist essentially of a PEG-NETS, for example, a 4-arm PEG-SG; a 4-arm PEG-amine or albumin; a triblock copolymer including a central block of PPG and two end blocks of PEG, and, a buffer solution having a pH in the range of about 8.5 to about 9.0.

The present disclosure further describes formulations of the liquid compositions as described above, that include one or more viscosifiers in combination with the previously described amphiphilic poly(alkyl)ene glycol block polymer. Viscosifiers are well known in the art of biocompatible sealants. Exemplary viscosifiers can include, for example, carrageenans (iota, kappa, and lambda), starch (including corn starch), cellulose (including carboxymethyl cellulose, hydroxypropyl methylcellulose, microcrystalline cellulose), alginate, agar (including agarose), glycerol, pectin (including apple pectin, citrus pectin), gum (including guar, gellan, xanthan, locust bean) and gelatin. According to certain embodiments, the viscosifier includes a mixture of at least two different viscosifier compounds. In further embodiments, the viscosifier includes at least one of carboxymethyl cellulose (CMC) or carrageenan, and in still further embodiments, includes a mixture of CMC and carrageenan.

According to embodiments of the present disclosure, the viscosifier is present in the composition in an amount in the range of about 0.1% to about 10% (w/v). In a preferred embodiment, the viscosifier is present in the composition in an amount in the range of about 0.1% to about 5.0% (w/v). In still further embodiments, the viscosifier is present in the composition in an amount in the range of about 0.1% to about 1.0% (w/v). In specific embodiments including a mixture of at least two viscosifier compounds, at least one of the viscosifier compounds in present in amount in the range of about 0.1% to about 1.0%.

As previously stated, in certain embodiments, at least two different viscosifiers can be combined for viscous synergism, where interaction with each other creates new textures and speeds thickening time. For example, ι-carrageenan, when combined with starch, can increase the viscosity of the solution by ten times the viscosity of a solution with starch alone. These synergies can potentially be very useful in liquid sealants according to the present disclosure for a dual benefit: 1) smaller concentrations of the additives that behave in synergy can be used, which may address potential toxicity issues with higher concentrations of a single additive; 2) smaller concentrations may also result in reduced costs.

Carrageenans are a family of high molecular weight linear polysaccharides composed of sodium, potassium, and magnesium and calcium sulphate esters of galactose and 3,6-anhydrogalactose copolymers. The viscosity of carrageenan solutions is dependent on molecular weight, concentration, and temperature, as well as the presence of other solutes, Carrageenan viscosity typically increases exponentially with concentration. There are three main types of carrageenan that differ in their respective degrees of sulfation: λ-carrageenan with three sulfate groups per disaccharide, ι-carrageenan with two and κ-carrageenan with one. Higher ester sulfates require lower temperatures to solubilize the additive.

While all three forms of carrageenan are water-soluble, dissolution is affected by type of carrageenan, counter ions, solutes, temperature, and pH. Due to the level of sulfation, λ-carrageenan is the most soluble of the three; ι-carrageenan is intermediate but behaves hydrophilic since its two-sulfate can counteract the less hydrophilic character of the 3,6-anhydrogalactose residue. Carrageenans are known to maintain good stability in neutral and alkaline pH, making them good potential additives for soft tissue liquid sealants, which are typically composed of moderately alkaline buffers.

Starch, a linear chain of glucose units connected by glycosidic bonds, has limited solubility, which can present issues to its use in standard sealant manufacturing processes. Isolated starch is practically insoluble in cold water, alcohols and most organic solvents because of hydrogen bonds and the molecule's crystallinity. Additionally, aggregation occurs readily as the polymers swell substantially upon contact with water. Temperature, pH, rate of heating, and the presence of other salts, all affect starches. Furthermore, shear forces and pressure-induced mixing can alter starch solubility and its final viscosity. To help improve solubility, small amounts of starch can be added to water to gelatinize or create a paste; followed by dilution, slowly adding more granules to reach desired concentration, along with heating.

Cellulose-derived carboxymethylcellulose (CMC) is composed of carboxymethyl groups bound to hydroxyl groups of the glucopyranose monomers along the cellulose backbone. The carboxymethyl group functions as an acid, making CMC an anionic polyelectrolyte. CMC is hydrophilic by nature and will swell in water, forming agglomerates and lumps. Shear forces applied during any mixing processes that include CMC can influence the final viscosity of the solution. Dissolution rate and viscosity can also be affected by concentration and temperature; and pH and electrolytes can have less of an influence. With temperature, the viscosity decreases as it goes up, although this is reversible, as the original viscosity can be restored when the temperature returns to the starting value. CMC is stable within a wide range of pH values; only at levels greater than 11 will cause an affect due to alkaline hydrolysis or levels less than 4 where the cation will be replaced by hydrogen and cause the molecule to become insoluble in water. Electrolytes effect on viscosity depends on the ability of the cation to form a soluble salt with the molecule; this depends on the concentration of the salt and CMC. The CMC molecule will coil and change configuration when exposed to electrolytes and in-turn decrease in viscosity.

Alginates are water-soluble hydrocolloid biopolymers. It is an anionic polymer composed of a linear backbone of homopolymeric blocks of (1-4)-linked β-D-mannuronate (M) and its C-5 epimer α-L-guluronate (G) residues. Alginate dissolution typically requires active stirring along with slow addition to the solvent to prevent lumping and flocculation. Pre-mixing with a liquid that alginate is insoluble in, such as alcohol or PEG, will enhance dispersion and facilitate dissolution. Concentration and temperature expectedly affect both dissolution and the final viscosity of the solution. Shear rate also plays a role as alginates possess a pseudo-plastic property, where viscosity decreases with increasing shear rate. Lastly, alginates are highly susceptible to microbial attack over other carbohydrate-based additives, and if compromised, will cause a reduction in viscosity.

In certain embodiments, the liquid compositions according to the present disclosure consist essentially of reactive hydrogel mixtures of an electrophilic compound and nucleophilic compound that are cross-linkable with each other via reaction of the available electrophilic and nucleophilic moieties of each compound; an amphiphilic poly(alkyl)ene glycol block polymer; a viscosifier and, a buffer solution having a pH in the range of about 8.5 to about 9.0. In preferred embodiments, the liquid compositions according to the present disclosure consist essentially of PEG-NHS, such as 4-arm PEG-SG; 4-arm PEG-amine or albumin; a triblock copolymer including a central block of PPG and two end blocks of PEG; a mixture of CMC, and ι-carrageenan; and, a buffer solution having a pH in the range of about 8.5 to about 9.0.

The present disclosure further describes systems for forming crosslinking sealants for use in the repair and treatment of soft tissues. According to certain embodiments, the systems can include a first container containing a first liquid and a second container containing a second liquid, where the first liquid has a buffer solution having a pH in the range of about 8.5 to about 9.0, a cross-linkable electrophilic compound, and an amphiphilic poly(alkyl)ene glycol block polymer; and, the second liquid has a buffer solution having a pH in the range of about 8.5 to about 9.0, and a cross-linkable nucleophilic compound. In the disclosed systems, the cross-linkable electrophilic compound and the cross-linkable nucleophilic compound are configured to form a cross-linked soft tissue sealant upon admixture of the first liquid and the second liquid.

The present disclosure additionally describes a surgical method of treating or repairing soft tissue, for example, pleural tissue that includes the steps of:

mixing a first liquid contained in a first container and a second liquid contained in a second container to form a liquid soft tissue sealant, where the first liquid includes a buffer solution having a pH in the range of about 8.5 to about 9.0, a cross-linkable electrophilic compound, and an amphiphilic poly(alkyl)ene glycol block polymer; and the second liquid includes a buffer solution having a pH in the range of about 8.5 to about 9.0, and a cross-linkable nucleophilic compound;

forming a liquid cross-linked tissue sealant from the mixture of the first and second fluids; and, applying the liquid cross-linked tissue sealant to cover a targeted pleural tissue surface.

EXAMPLES

Example 1: Effect on Ultimate Elongation and Ultimate Stress in Modified Base Sealant Formulations (Bio-Synthetic)

Materials

Base formulation—75 mg/mL 4 Arm PEG-SG-20k (electrophile), 10% albumin (nucleophile), 50 mM carbonate buffer, pH=9.0

Additives—0.1% ι-carrageenan (viscosifier), 1% carboxymethylcellulose (viscosifier), 5% Poloxamer 407 (amphiphilic poly(alkyl)ene glycol block polymer) (Approx. MW=12.6 kD).

In a first run, three (3) samples of the base formulation were measured for ultimate extension, against two separate formulations including viscosifier compounds—four (4) samples including the base formulation and 0.1% ι-carrageenan, and five (5) samples including the base formulation and 1.0% CMC.

In a second run, ten (10) sample of the base formulation were measured for ultimate extension against three (3) samples including the base formulation and 5% Poloxamer 407.

In the third run, ten (10) sample of the base formulation were measured for ultimate extension against three (3) samples including the base formulation and 5% Poloxamer 407, and four (4) samples including the base formulation, 5% Poloxamer, and 1% CMC/0.2% ι-carrageenan.

In the fourth run, ten (10) sample of the base formulation were measured for ultimate stress against three (3) samples including the base formulation and 5% Poloxamer 407, and four (4) samples including the base formulation, 5% Poloxamer, and 1% CMC/0.2% ι-carrageenan.

For this study, the cure time of the sealants tested was 10 minutes.

The ultimate stress, ultimate strain, and elastic modulus were calculated in MATLAB R2018. Statistical analyses were performed in Minitab v18. The tensile test measured the elongation at complete failure of the sealant when tested in a vertical, tensile direction at 5 mm/min. Custom fixtures, fabricated from Teflon, were designed to create a 'dog bone' shape and to express the sealant into, which allowed them to be mounted to an Instron Materials Tester. As the crosshead moves vertically, the fixtures pull apart, measuring the strength and elongation for each sample. The failure was defined as the point at which the sealant completely failed within the fixture.

Figure 1C:
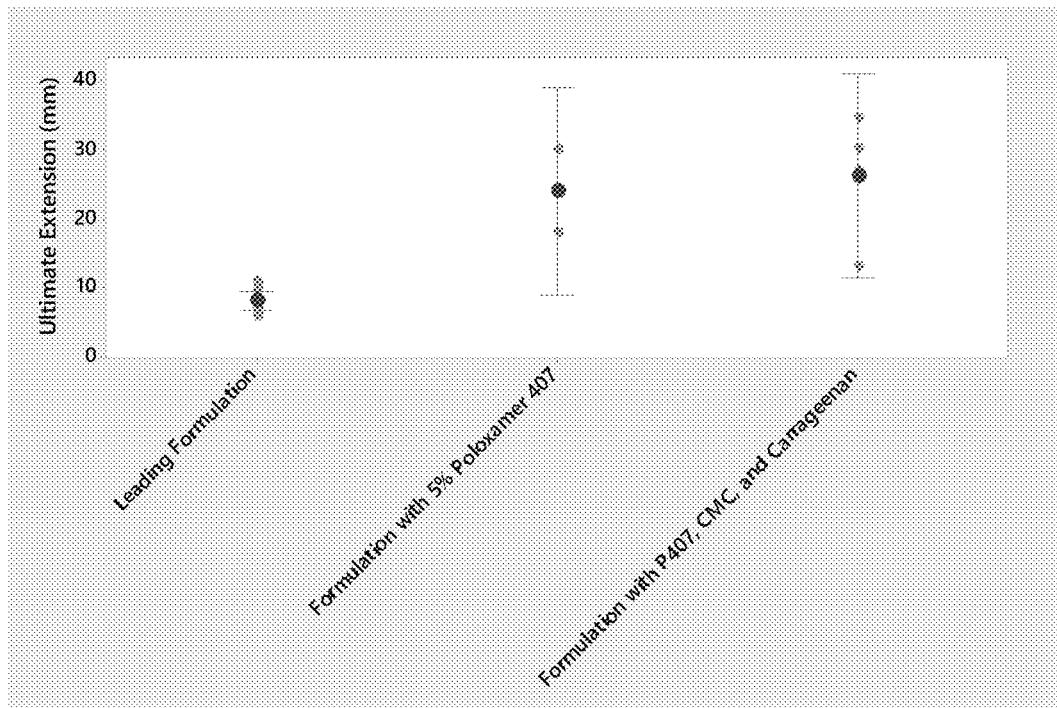
FIG. 1C is a graphical representation of ultimate extension of the samples from FIG. 1B, and an additional sample according to the present disclosure including the amphiphilic poly(alkyl)ene glycol block polymer (Poloxamer 407) and a viscosifier.
Figure 1D:
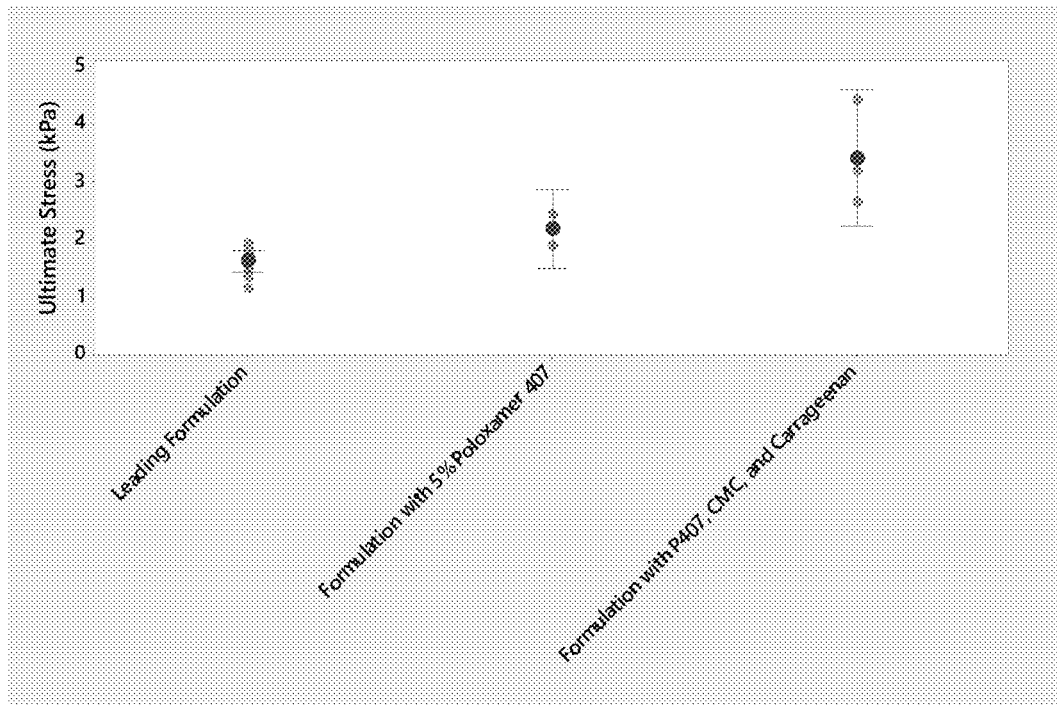
FIG. 1D is a graphical representation of ultimate stress of the samples measured in FIG. 1C.

The results are shown in FIG. 1A-1D. Referring to FIG. 1A, there was no statistically measurable difference in ultimate extension among the three formulations from the first run (2 sample t-test) Referring to FIG. 1B, in the second run, the ultimate extension between the two groups was statistically different (p=0.046, 2-sample t-test) showing an increased ultimate extension for the samples including the Poloxamer 407. Referring to FIG. 1C, similar to the results shown in FIG. 1B, there was a statistically significant difference in ultimate extension between the base formulation, and the two formulations including the Poloxamer 407; however, there was no statistical change in ultimate extension between the two formulations with the Poloxamer 407 with the addition of the viscosifier (one-way ANOVA analysis). Finally, with reference to FIG. 1D, there was a statistically significant increase in the ultimate stress of the samples tested that included the viscosifier, as compared to the two formulation that did not have the viscosifier (p=0.00, one-way ANOVA).

Example 2: Effect of Varying Amphiphilic Poly(Alkyl)Ene Glycol Block Polymer Concentration on Tensile Properties of Sealant Formulation (Bio-Synthetic)

Pluronic F127 (amphiphilic poly(alkyl)ene glycol block polymer) [BASF trade name for Poloxamer 407 previously described above] was dissolved in 100 mM carbonate buffer (pH=8.0) at 0, 0.1, 0.3, 2, 5, 10, 15, 20, 25, and 30% (w/v). 5 mL of the Pluronic solution was added to 750 mg PEG-SG4-20k and allowed to dissolve for 5 min. The solution was loaded into 20 mL syringe and attached to a 20 mL syringe with 5 mL of 20% albumin (dissolved in water) via a dual syringe connector. The solutions were passed back and forth 10 times to generate the sealant. The sealant was immediately injected into the tensile molds for testing.

The tensile test measures the elongation at complete failure of the sealant when tested in a vertical, tensile direction at 5 mm/min. Custom fixtures, fabricated from Teflon, were designed to create a 'dog bone' shape and to express the sealant into, which allowed them to be mounted to an Instron Materials Tester.

As the crosshead moves vertically, the fixtures pull apart, measuring the strength and elongation for each sample. The failure was defined as the point at which the sealant completely failed within the fixture.

For this study, the cure time of the sealants tested was 10 minutes. The ultimate stress, ultimate strain, and elastic modulus were calculated in MATLAB 82018. A one-way ANOVA was performed to provide statistical comparisons between groups.

Figure 2A:
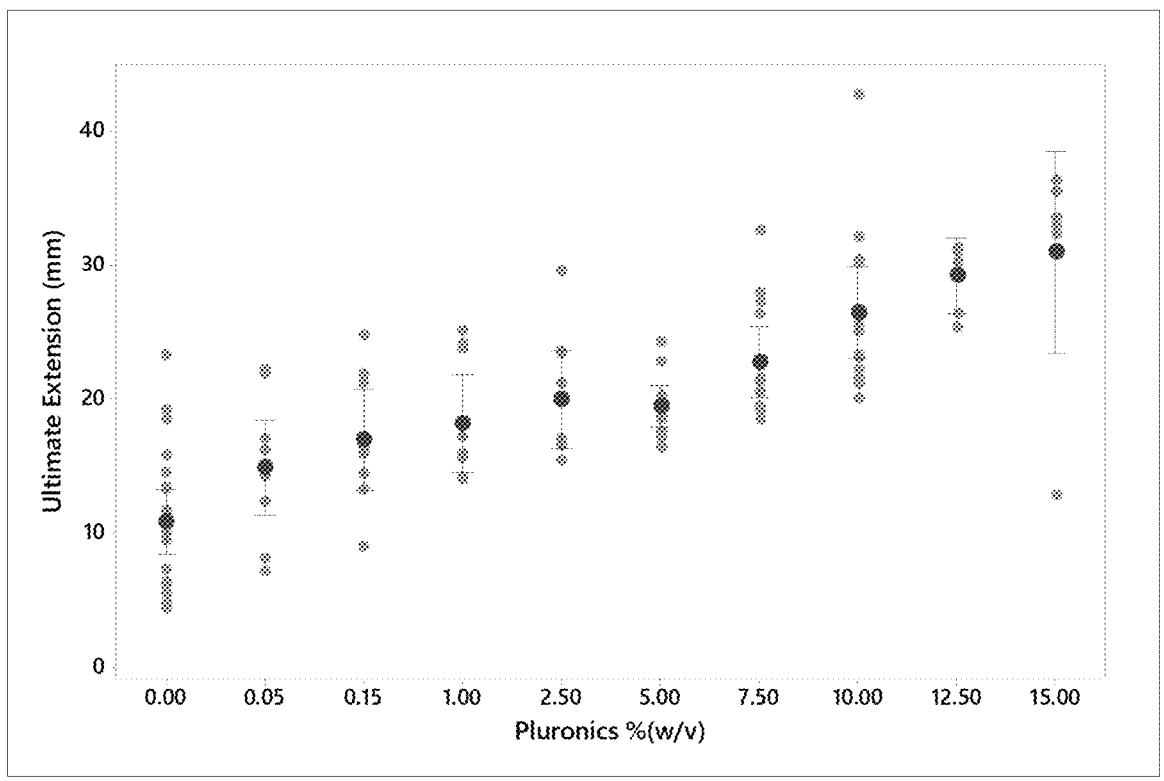
FIGS. 2A-2B are graphical representations of ultimate extension and ultimate stress of sample according to the present disclosure over various concentrations of the amphiphilic poly(alkyl)ene glycol block polymer (Poloxamer 407)
Figure 2B:
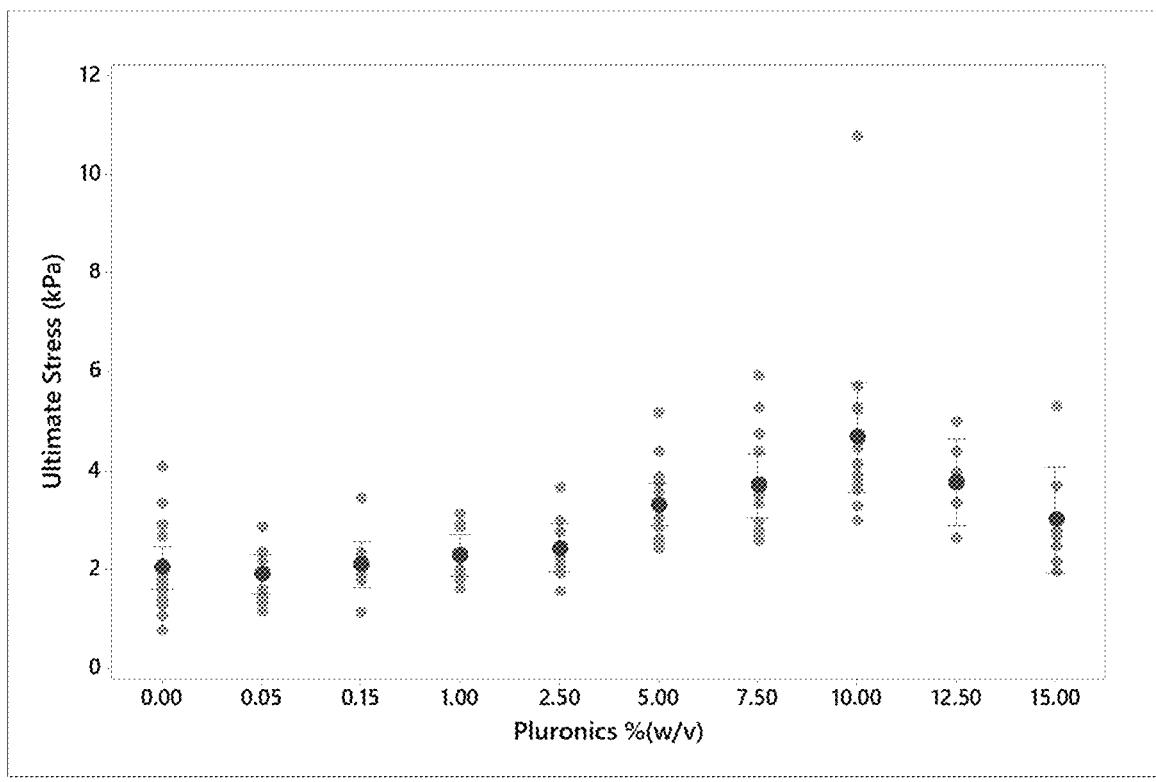

With reference to FIG. 2A, there was a significant increase in ultimate extension (p<0.01, one-way ANOVA, Appendix) with increasing concentration of Pluronic F127. With reference to FIG. 2B, ultimate stress (p<0.01, one-way ANOVA, Appendix) values increased to a maximum at approximately 10% concentration and then a subsequent decrease with further Pluronic F127 concentration. Although the ultimate extension increased on average over the entire range of concentrations tested, the ultimate stress was statistically increased between the concentration of 5% and 15%, and maximized between 7.5% and 12.5%.

Example 3: Effect of Amphiphilic Poly(Alkyl)Ene Glycol Block Polymer Concentration on Tensile Properties of Sealant Formulation (Fully Synthetic)

Materials

TABLE 1

| 4 Arm PEG-Amine-5k (mg/mL) | 4 Arm PEG-SG-20k (mg/mL) | Pluronics F127 (mg/mL) |
| --- | --- | --- |
| 28.5 | 75 | 0 |
| 57.0 | 150 | 4 |
| 114.0 | | |

A 3 factor, general factorial design was utilized in this study. The PEG-Amine was tested at 3 levels and the PEG-SG and Pluronics were tested at two levels. The Pluronics F127 was dissolved in 100 mM carbonate buffer (pH=8.0). 5 mL of the Pluronic solution was added to 750 mg PEG-SG4-20k and allowed to dissolve for 5 min. The solution was loaded into 20 mL syringe and attached to a 20 mL syringe with 5 mL of the PEG-Amine solution via a dual syringe connector. The solutions were passed back and forth 10 times to generate the sealant. The sealant was immediately injected into the tensile molds for testing.

The tensile test measures the elongation at complete failure of the sealant when tested in a vertical, tensile direction at 5 mm/min. Custom fixtures, fabricated from Teflon instead of aluminum, were designed to create a 'dog bone' shape and to express the sealant into, which allowed them to be mounted to an Instron Materials Tester. As the crosshead moves vertically, the fixtures pull apart, measuring the strength and elongation for each sample. The failure was defined as the point at which the sealant completely failed within the fixture.

For this study, the cure time of the sealants tested was 10 minutes. The ultimate stress, ultimate strain, and elastic modulus were calculated in MATLAB 82018. Statistical analyses were performed in Minitab v18.

Figure 3A:
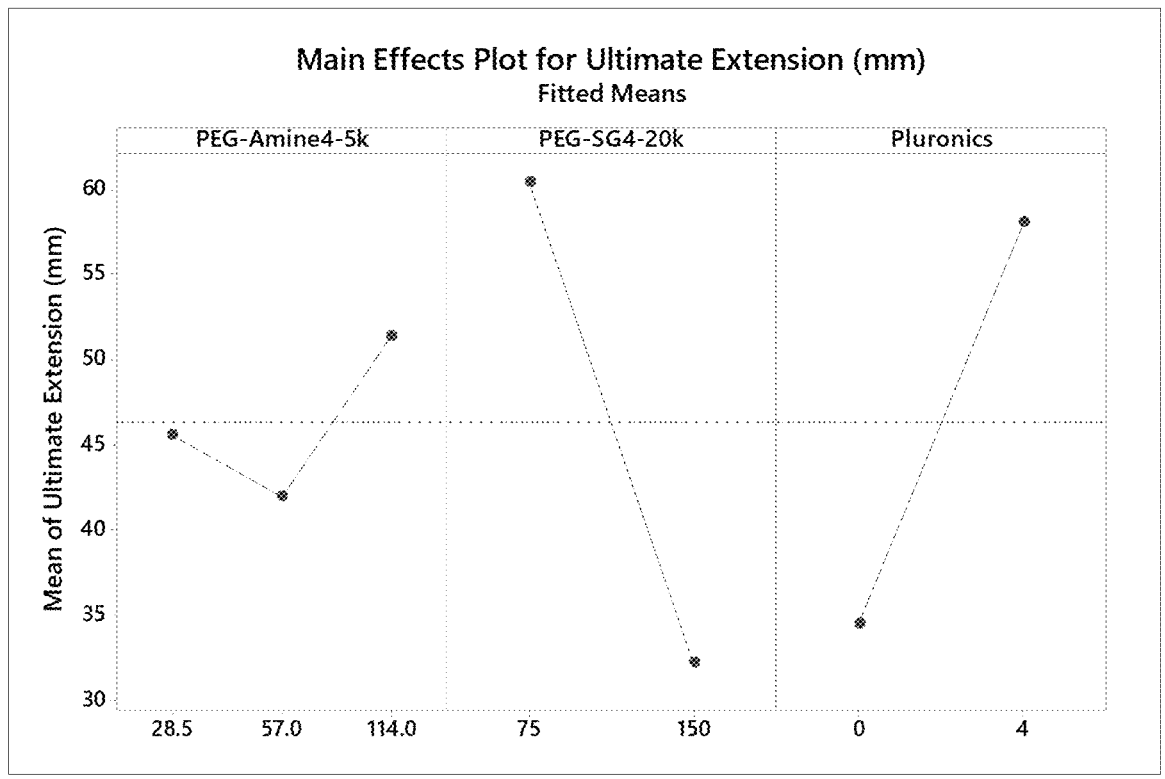
FIGS. 3A-3C are graphical representations of ultimate extension, ultimate stress, and stiffness displayed as fitted means for varying the concentrations of the electrophilic compound and the amphiphilic poly(alkyl)ene glycol block polymer.
Figure 3B:
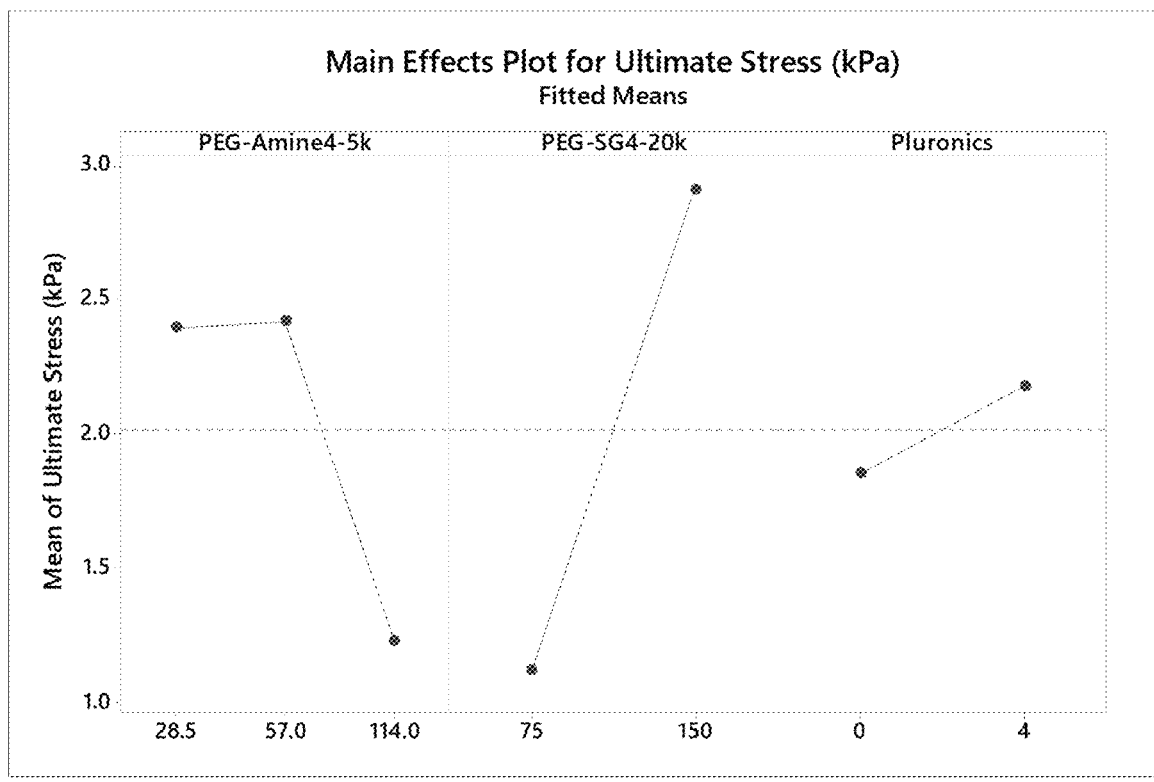
Figure 3C:
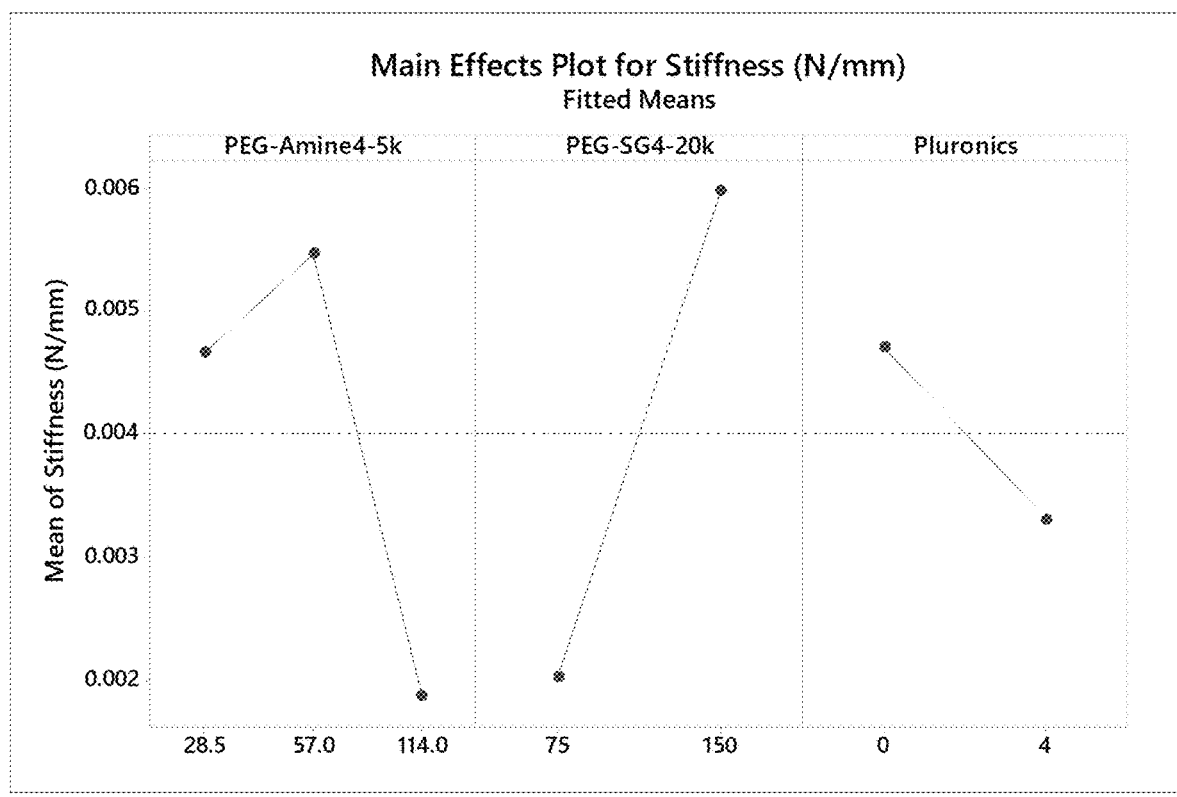

With reference to FIGS. 3A-3C, an analysis of the main effects showed that as PEG-SG decreased and Pluronics increased, the ultimate extension of the formulation increased. As PEG-SG increased and Pluronics increased, the ultimate stress increased. As PEG-SG increased and Pluronics decreased, the stiffness increased. On the other hand, PEG-Amine did not affect the tensile properties in a linear fashion. As the concentration of PEG-Amine increased from 28.5 to 57 mg/mL, the properties did not change a great deal; however, from 57 to 114 mg/mL the ultimate extension increased, and the ultimate stress and stiffness decreased substantially. The results showed PEG-SG, Pluronics, and their interaction had a significant effect on ultimate extension. PEG-Amine and PEG-SG had a significant effect on ultimate stress. PEG-Amine, PEG-SG, and Pluronics had a significant effect on stiffness.

Example 4: Analysis of Viscosifier Formulations

This study investigated individual viscosity-enhancing additives and their combinations with the control formulation while maintaining or improving functional material properties.

Materials—The components used in the formulations tested below are as follows:
- PEG-SG (4arm), MW: 20 kDa, [Jenkem]
- Bovine Serum Albumin, [Sigma A7030]
- Sodium Carbonate, [Sigma 223484]
- ι-Carrageenan, [TCI C1805]
- λ-Carrageenan, [TCI C3313]
- Ultra-Sperse® Corn Starch, [Ingredion]
- Carboxymethylcellulose (CMC) sodium salt (HV), [Sigma C5013]
- Alginic acid sodium salt from brown algae, [Sigma A2033]
- Pluronic® F-127, [Sigma P2443]

Example 4A: Preparation of Liquid Sealant Groups

Ten liquid sealant additive groups or additive combination groups were used for this study; a control condition without any additive was composed of PEG-SG4-20K. For each experimental group, at least three concentrations of the additive(s) were first qualitatively evaluated for ease of dissolution and generating/maintaining enhanced viscosity in carbonate buffer (pH 9.0). Conditions that required excessively high temperatures (e.g., >5% starch), had undissolved solutes (e.g., >5% starch), or generated bubbles (e.g., >20% Pluronic F-127) were eliminated. Minor modifications to the experimental groups and/or additional controls were generated and used in different evaluations depending on the subset-objective. Table 2 below shows the prepared sealant compositions for testing.

TABLE 2

Formulation List for Testing

| Test Group | Additive and PEG Solution (Syr. 1) | Albumin Solution (Syr. 2) |
|---|---|---|
| ELS (control) | 150 mg/mL PEG-SG4-20K, 100 mM CB (pH 9.0) | 20% BSA |
| ι-Carr | 150 mg/mL PEG-SG4-20K, 100 mM CB (pH 9.0), 0.25% ι-carrageenan (TCI) | 20% BSA |
| ι-Carr | 150 mg/mL PEG-SG4-10K, 100 mM CB (pH 9.0), 0.25% ι-carrageenan (TCI) | 20% BSA |
| Starch | 150 mg/mL PEG-SG4-20K, 100 mM CB (pH 9.0), 5.0% corn starch | 20% BSA |
| CMC | 150 mg/mL PEG-SG4-20K, 100 mM CB (pH 9.0), 2% CMC (HV) | 20% BSA |
| Alginate | 150 mg/mL PEG-SG4-20K, 100 mM CB (pH 9.0), 3% Alginate (MV) | 20% BSA |
| ι-Carr + λ-Carr | 150 mg/mL PEG-SG4-20K, 100 mM CB (pH 9.0), 0.25% ι-carrageenan (TCI), 0.75% λ-carrageenan | 20% BSA |
| ι-Carr + Starch | 150 mg/mL PEG-SG4-20K, 100 mM CB (pH 9.0), 0.25% ι-carrageenan (TCI), 3% starch | 20% BSA |
| CMC + λ-Carr | 150 mg/mL PEG-SG4-20K, 100 mM CB (pH 9.0), 1% CMC (HV), 0.75% λ-carrageenan | 20% BSA |
| Alginate + λ-Carr | 150 mg/mL PEG-SG4-20K, 100 mM CB (pH 9.0), 1% Alginate (MV), 0.75% λ-carrageenan | 20% BSA |
| F127 + CMC + ι-Carr | 150 mg/mL PEG-SG4-20K, 100 mM CB (pH 9.0), 10% F127, 1% CMC (HV), 0.20% ι-carrageenan (TCI) | 20% BSA |

Example 4B: Assessing Dissolution

Additives and additive combination groups were added to carbonate buffer to first evaluate ease or difficulty of dissolution and compare within the groups. A semi-quantitative scoring system from 1 to 3 was generated to assess the number of steps; a score of 1 indicated a 1 step process, 2 for 1-2 steps, and 3 for >3 steps, which is shown below in Table 3. As an example, the 5% starch group had a score of 3 since dissolution required slowly adding the powder through a funnel to a boiling carbonate buffer liquid solution that was in motion/vortex formed by a stirrer (3 step process requiring particle wetting, rapid mixing, and high heat). All additives in this study were found to result in severe agglomeration and lumping if added directly to carbonate buffer. Gentle addition for individual particle wetting, stirring/vortex, heat and/or time were necessary to a certain degree for all additives (some more than others). Starch, CMC, alginate, and any combinations incorporating starch were the most labor-intensive and challenging to fully solubilize. Starch, in most cases, required boiling temperatures to full dissolve, making it a poor choice for an additive from a processing standpoint.

TABLE 3

Additive Dissolution Scoring
(1 = 1 step, 2 = 1-2 steps, 3 = >2 steps)

| Sample | Dissolution Scoring |
|---|---|
| ELS (control) | 1 |
| 0.25% ι-Carr | 2 |
| 5% Starch | 3 |
| 2% CMC | 3 |
| 3% Alginate | 3 |
| 0.25% ι-Carr + 0.75% λ-Carr | 2 |
| 0.25% ι-Carr + 3% Starch | 3 |
| 0.75% λ-Carr + 1% CMC | 2 |
| 0.75% λ-Carr + 1% Alginate | 2 |
| 10% F127 + 0.2% ι-Carr + 1% CMC | 2 |

Example 4C: Assessing Hydration (FIG. 4)

PEG-SG4-20K powder was added to the viscosity-enhanced carbonate buffer to create a 150 mg/mL solution. The solution was mixed via dual-syringe exchange using 5 mL BD syringes and a female-to-female connector. To assess hydration time, the number of pumps required to visually dissolve the PEG was noted as a rate measure. For consistency in measurement, only one operator performed this test and passed each syringe at a rate of 1 pump/2 seconds. A virtual metronome was used as a guide to maintain precision.

Figure 4:
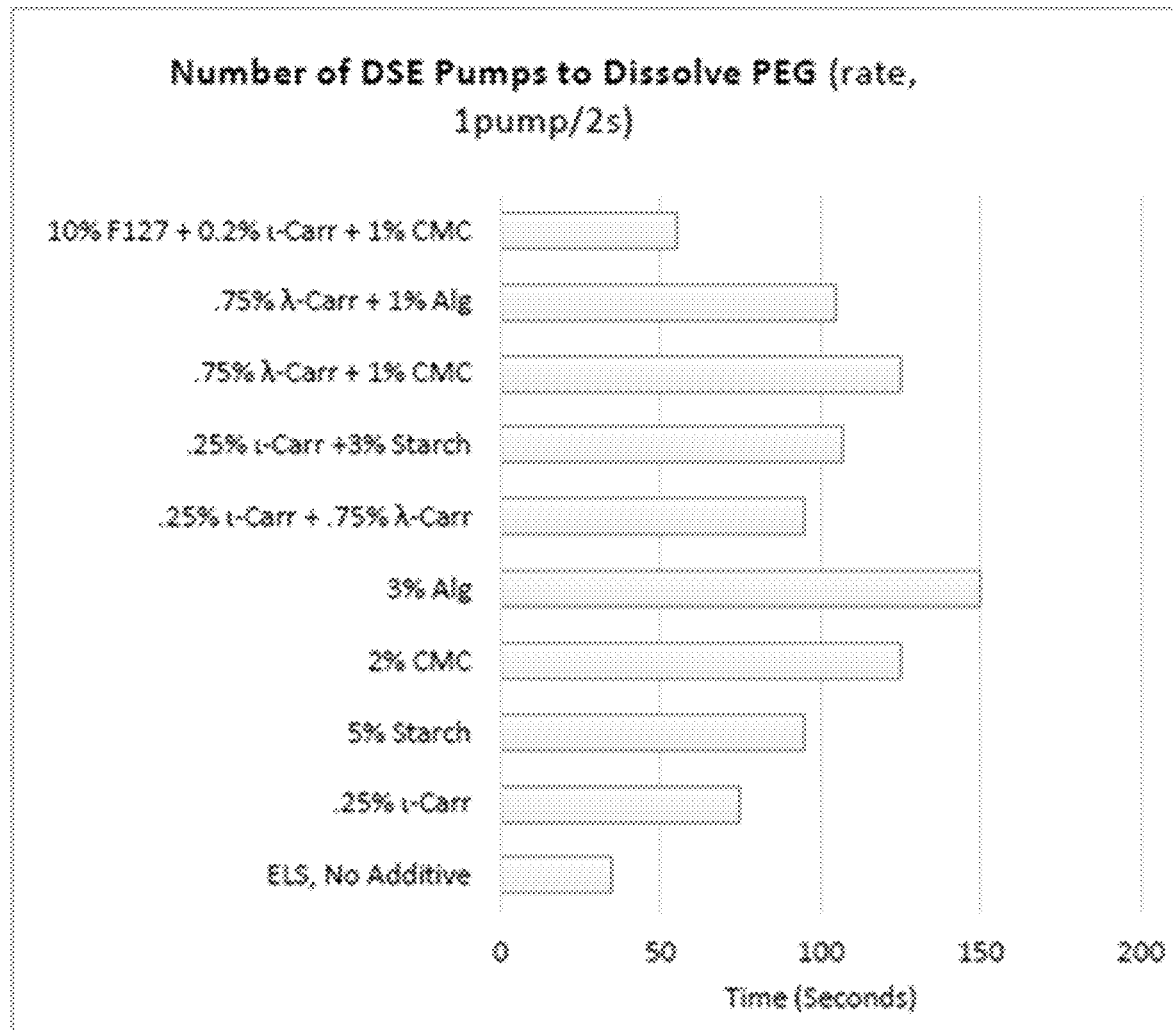
FIG. 4 is a graphical representation of time for dissolution of samples according to the present disclosure.

Hydration time for PEG-SG4-20K powder in the viscosity-enhanced carbonate buffer by dual-syringe exchange varied with the type of additive, which can be seen in FIG. 4. The 3% alginate and 2% CMC conditions took the longest (greater than 2 minutes). This time frame has the potential to be problematic in a clinical setting. Unexpectedly, certain additive-combination groups such as 0.25% ι-carrageenan and 0.75% λ-carrageenan dissolved the PEG relatively fast, despite showcasing a high level of dynamic viscosity.

Example 4D: Assessing Polymerization

Figure 5:
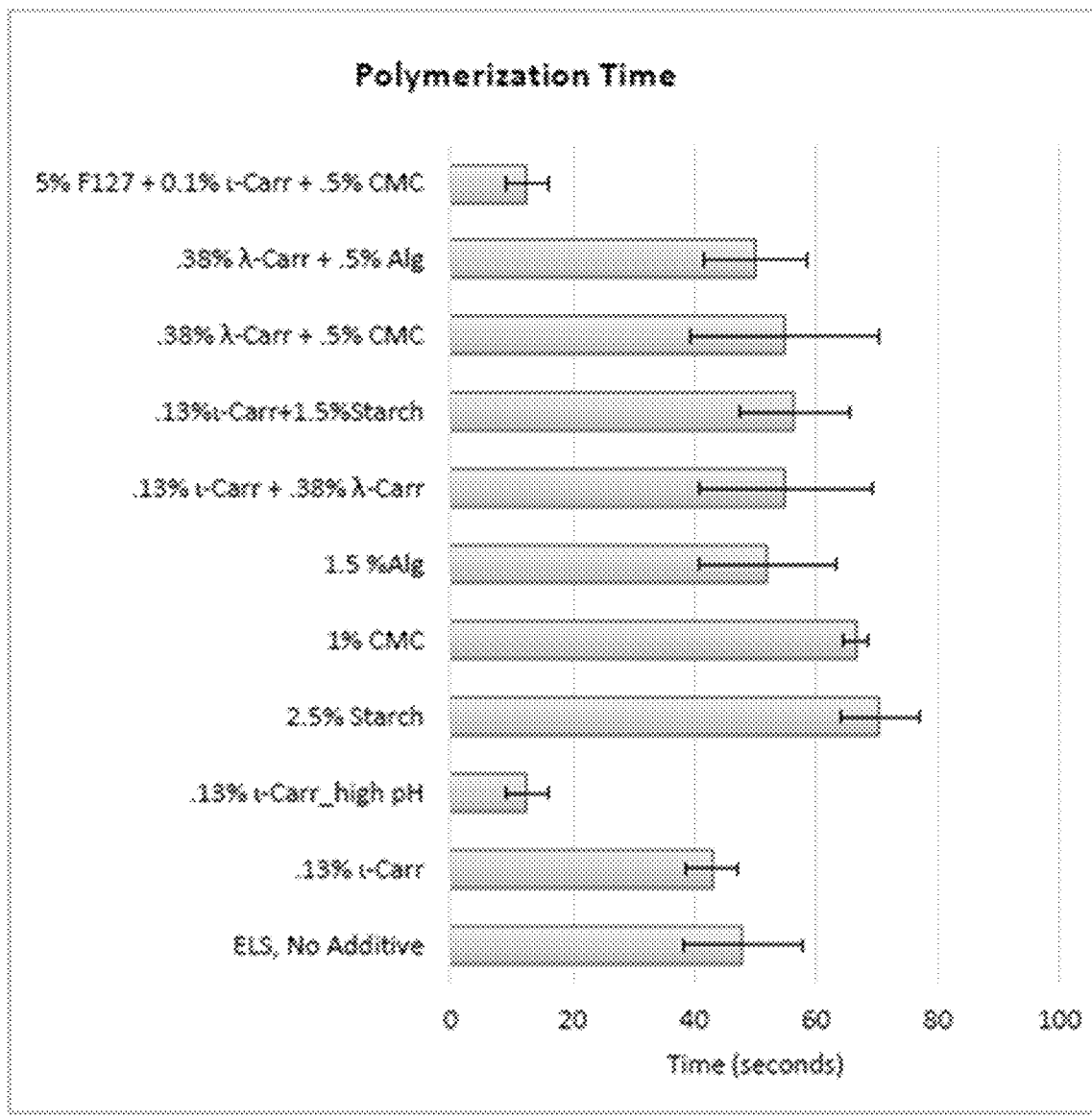
FIG. 5 is a graphical representation of time for polymerization of samples according to the present disclosure.

To express the actual sealant, the respective viscosity-enhanced 150 mg/mL PEG-SG4-20K solution and 20% bovine serum albumin (BSA) formulations were loaded into an Evicel delivery device attached to a prototype alternating viscous mixing tip. 1 mL of the sealant was expressed into a 1" weigh boat containing a 6 mm silicone bead, on a nutating rocker at 20 degrees. The time it took for the bead to stop moving reflected the polymerization time for the respective condition. This procedure was conducted with duplicates (n=2) for each condition. The results for each tested sample are shown in FIG. 5.

Polymerization time, in general, was relatively reasonable for all viscous sealant groups as gelling was complete in under 75 seconds or less. In order to provide a suitable clinical target time, preferably, 30 seconds or less, certain of these formulations may require additional modifications (e.g., concentrations, pH alteration, and mixing) in order to reduce polymerization time. For example, an additional 0.13% i-carrageenan formulation with a higher pH was tested in this experiment as a secondary control; the higher pH resulted in substantially faster polymerization with a mean time of 12.5 seconds. Without being bound by any particular theory, raising pH may be a factor to reduce and control polymerization time.

Example 4E: Sealant Flowrate, Stopping Distance & Expression

Sealant flowrate and stopping distance provide important information on flowability of viscous sealants. While reducing flowrate is a primary objective for the liquid sealant, a highly viscous sealant will be subpar (or ineffective) if the additive largely affects polymerization time (resulting in larger stopping distances).

After loading the respective samples and 20% bovine serum albumin (BSA) into an Evicel delivery device attached to a prototype alternating viscous-mixing tip, 2 mL of the sealant was expressed onto a 15-degree glass-incline plane in triplicates (n=3). Flow rate and distance were captured and calculated by photo and video, respectively, as a camera was positioned perpendicular to the surface of the inclined plane. The flowrate was reported in inches per second, and the stopping distance in inches (6 inches=maximum distance of the plane).

Figure 6:
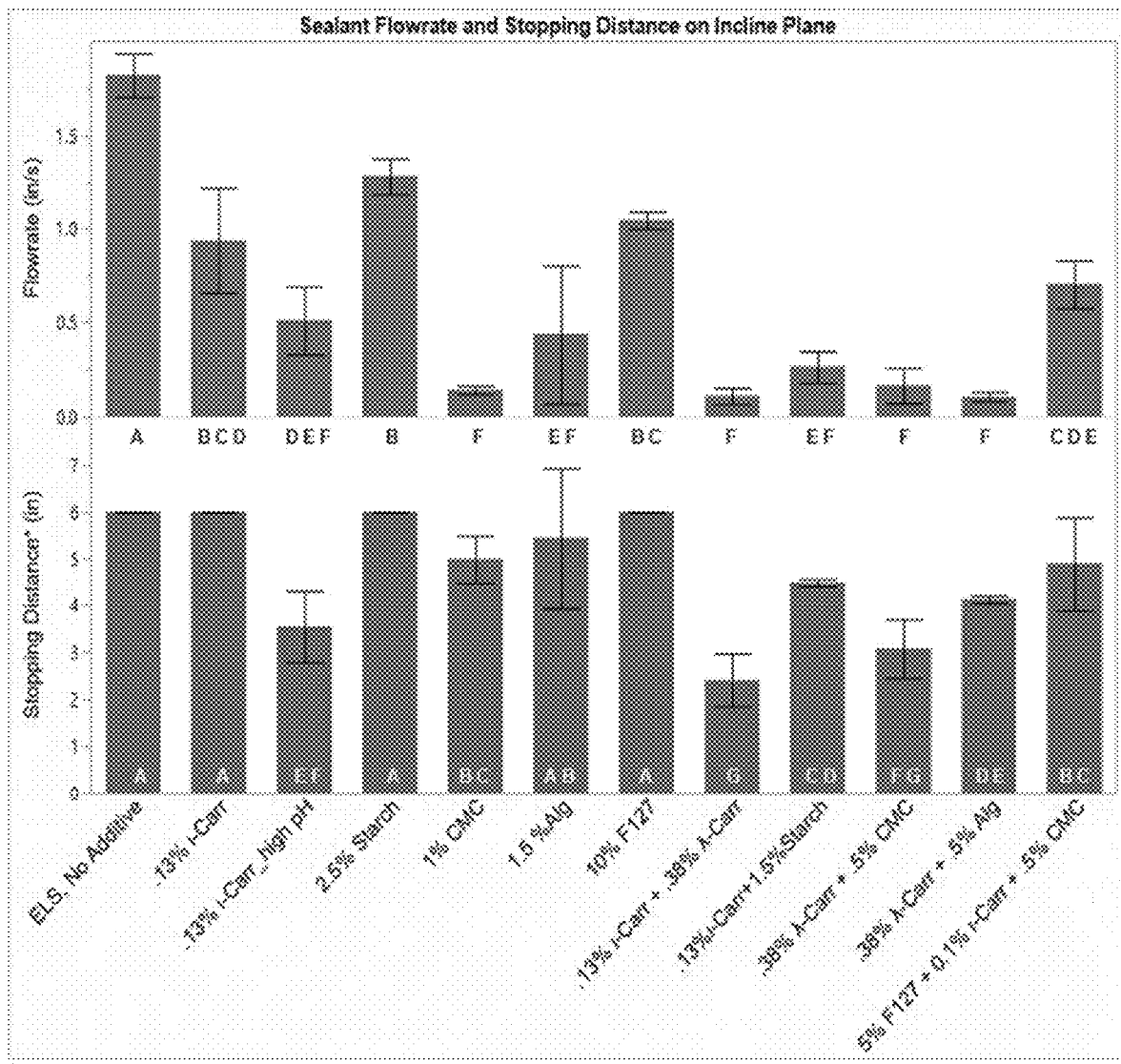
FIG. 6 is a graphical representation of sealant flowrate and stopping distance of samples according to the present disclosure.

Referring to FIG. 6, the viscosifier formulations, in comparison to the control, had a substantially lower flow rate, however this did not result in a corresponding reduced stopping distance for those samples (Each error bar is constructed using a 95% confidence interval of the mean. Sample size, n=3 for each group). Some sealant groups with high concentrations of a viscosifier (e.g., 1% CMC), while having relatively higher viscosity, gradually flowed to longer distances. However, other formulations, like 2.5% starch performed poorly in both assessments. Unexpectedly, the formulations including more than one viscosifier (each with relatively low concentrations) generally performed better in that they produced a very low flowrate, without compromising polymerization, as reflected by a short stopping distance.

During the course of the above testing, the expression force, thickness, and stretch/strength of the individual formulations were semi-quantitatively assessed on a scale from 1-3. While expression force was based on haptic feedback, thickness was measured at the top of the incline, after sealant was carefully separated from the glass. Stretch (elongation) & strength (resistance to breaking point) was haptic in nature as well and was qualitatively assessed by hand, after sealant was carefully separated from the glass. For expression force and stretch/strength, a score of 1 was the lowest and 3 the highest level. For thickness, a score of 1 indicated a measurement of <0.6 mm; 2 was 0.6-1 mm; and, 3 was >1 mm. Results are shown in Table 3 below:

TABLE 4

| Sample | Expression Force<br>1 = low<br>2 = medium<br>3 = high | Thickness<br>1 = <0.5 mm<br>2 = 0.5 mm-1.0 mm<br>3 = >1.0 mm | Stretch/Strength<br>1 = low<br>2 = medium<br>3 = high |
|---|---|---|---|
| ELS (control) | 1 | 1 | 2, 2 |
| 0.13% ι-Carr | 1 | 2 | 2, 2 |
| 0.13% ι-Carr (high pH) | 1 | 2 | 2, 2 |
| 2.5% Starch | 2 | 1 | 2, 1 |
| 0.5% CMC | 3 | 2 | 2, 2 |
| 1.5% Alginate | 3 | 2 | 3, 3 |
| 10% F127 | 2 | 1 | 3, 3 |
| 0.13% ι-Carr/0.38% λ-Carr | 3 | 3 | 3, 2 |
| 0.13% ι-Carr/1.5% Starch | 2 | 2 | 3, 1 |
| 0.38% λ-Carr/0.5% CMC | 3 | 3 | 3, 3 |
| 0.38% λ-Carr/0.5% Alginate | 3 | 3 | 3, 3 |
| 5% F127/0.1% ι-Carr/0.5% CMC | 2 | 2 | 3+, 3+ |

The expression force of the various viscosifier formulations, and the hydrogel thickness and stretch/strength provided important characteristic insights and distinctions from the control. Formulations with CMC and alginate (alone and in combinations) had the highest expression force values. In some cases, this resulted in thicker coatings. Although qualitative, some of these groups also resulted in high stretch/strength. Unexpectedly, the formulation including F127 and a viscosifier had a stretch/strength degree that surpassed every other tested formulation.

Example 4F: Tensile Properties for Viscous Liquid Sealants

The tensile test measures the tensile strength and elongation at complete failure of the sealant when tested in a vertical, tensile direction at 5 mm/min. Custom fixtures were fabricated from Teflon, designed to create a 'dog bone' shape to express the sealant into, which allowed them to be mounted to an Instron Materials Tester. Each of the viscous sealant groups were expressed in these fixtures using the Evicel delivery device attached to a prototype alternating viscous-mixing tip for testing. As the crosshead moves vertically, the fixtures pull apart, measuring the strength and elongation for each sample. The failure was defined as the point at which the sealant completely failed within the fixture. At least three samples were tested for each group (n>3).

Figure 7:
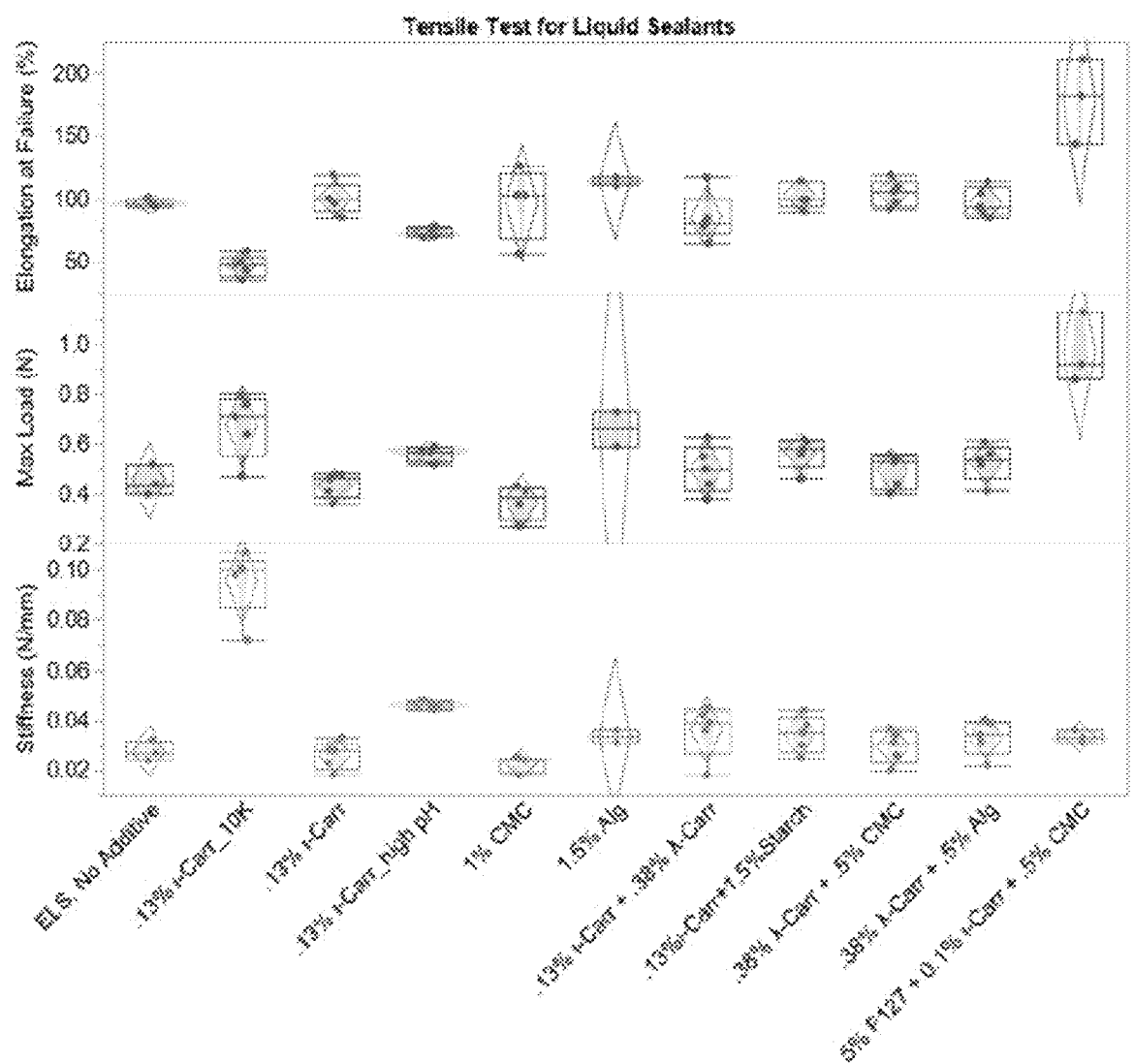
FIG. 7 is a boxplot showing tensile test data on elongation, max load, and stiffness for samples according to the present disclosure.
Figure 8:
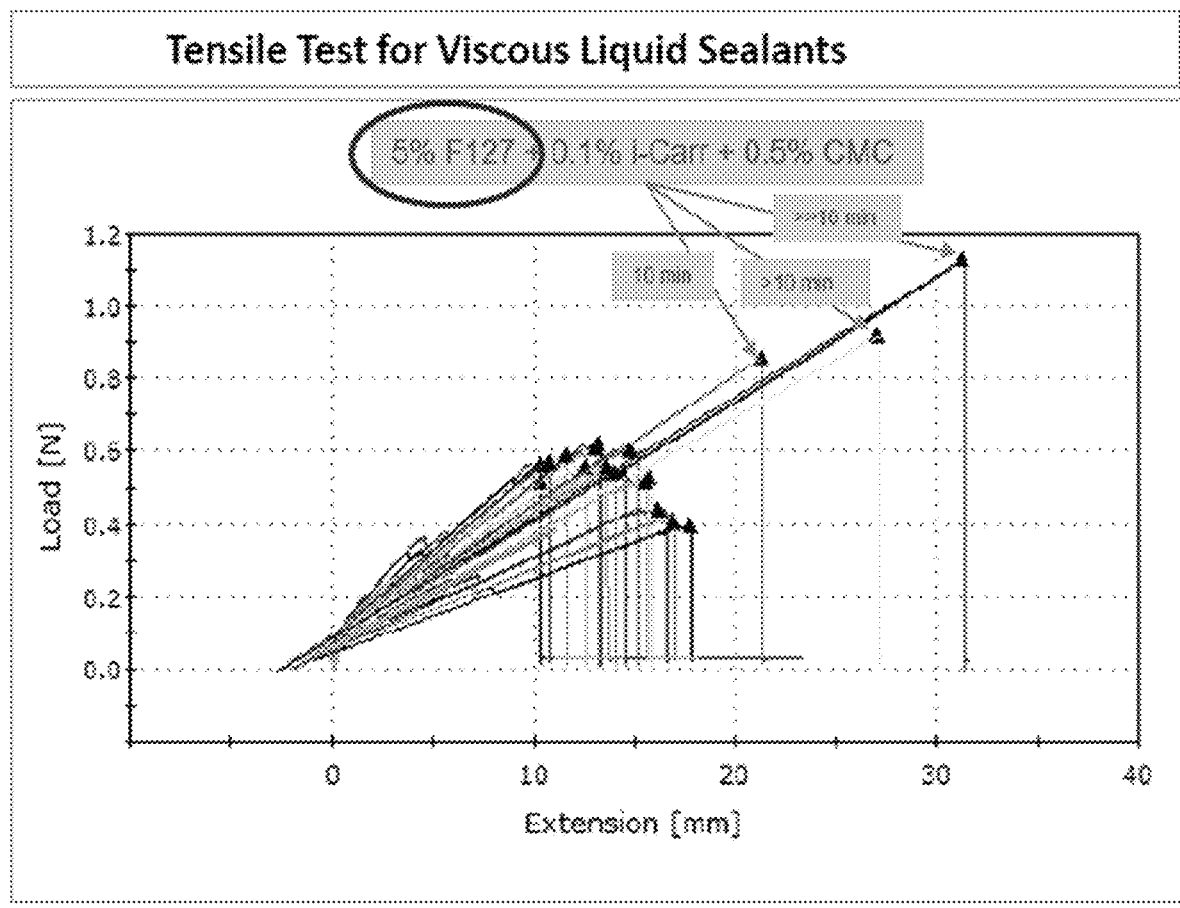
FIG. 8 is a graphical representation of load-extension curves of tensile testing for samples according to the present disclosure.

Tensile tests provide important distinctions and information on the biomaterial properties of elongation and stiffness for the viscous liquid sealants. Referring to FIG. 7, a boxplot is shown with the results of tensile test data on elongation, max load, and stiffness for sample formulations. For elongation, the test revealed two groups that were different from the rest of the formulations: the "ι-Carr, 10K" and "F127+CMC+ι-Carr" groups. The "ι-Carr, 10K" formulation, performed poorly in comparison to the rest of the samples with a significantly lower percent of elongation at failure. In contrast, the "F127+CMC+ι-Carr" formulation had a significantly higher percent of elongation than the other formulations. To further illustrate this unexpected improvement, FIG. 8 shows a comparison load-extension curves for all samples tested above, in which the 3 samples from the group with F127 poloxamer show an unexpectedly significant superiority to the other formulations. The test was performed sequentially on three samples for each group at a 10-minute cure time and then again after the 10-minute cure-time, which showed continued further improvement after curing. The "F127+CMC+ι-Carr" formulation had a mean elongation that was higher than the control, as well as the other formulations.

Example 4G: Tissue Adhesion Properties for Viscous Liquid Sealants

The tissue adhesion test measures the maximum adhesive load of the sealant between two tissue surfaces in a normal direction Testing was conducted following ASTM F2258-05. Certain modifications to the ASTM test protocol included round platens (1 square inch area) and a 3 mm gap between the two platen surfaces: Porcine pleura samples (Farm to Pharm—Warren, NJ) were mounted to the platens and the test fixtures were mounted to an Instron Materials Tester. Each of the viscous sealant formulations were expressed in these fixtures using the Evicel delivery device attached to a prototype alternating viscous-mixing tip for testing. A low-capacity load cell was used to assess the force between the two tissue surfaces. Upon starting the test, the crosshead of the Instron moved in a vertical direction at a rate of 5 mm/min until failure. The failure modes were defined as cohesive—failure within the foam, or adhesive—failure at the foam and tissue interface.

Figure 9:
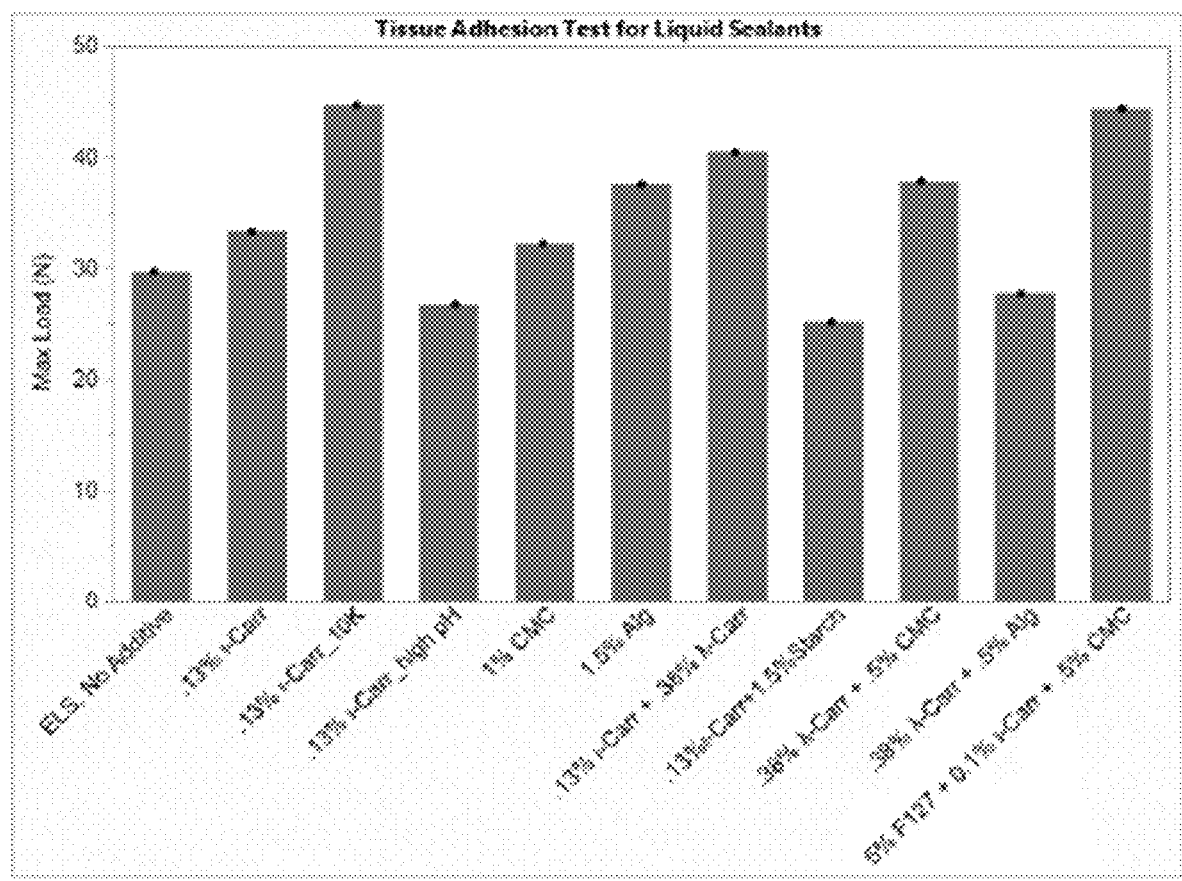
FIG. 9 is a graphical representation of tissue adhesion under maximum load for samples according to the present disclosure; and, FIG. 10 is a boxplot showing burst test data for samples according to the present disclosure.

Referring to FIG. 9, the results from tissue adhesion tests showed the "ι-Carr, 10K", "ι-Carr+λ-Carr" and "F127+CMC+ι-Carr" performed at least 25% better than the ELS control. While the "ι-Carr, 10K" group was expected to withstand higher loads given that previous findings had confirmed sealant formulations with PEG-SG4-10K were stiffer, the other formulations contained additives that not only improve viscosity, but also benefited tissue adhesion. As shown below in Table 5, failure modes, in almost all cases, were cohesive. For the group with F127, it may be important to note that "o-ring failure" of the fixture occurred at a point where no visual deformation was even evident at the tissue-sealant interface; this may suggest the formulation can withstand even higher loads than what was recorded.

TABLE 5

| | Failure Mode |
|---|---|
| ELS, no additive | Cohesive/Partially Adhesive |
| ι-Carr | Cohesive |
| ι-Carr, 10k | Cohesive |
| ι-Carr, high pH | Cohesive |
| CMC | Cohesive |
| Alginate (DSE) | Cohesive |
| ι-Carr + Starch | Cohesive |
| ι-Carr + λ-Carr | Cohesive |
| CMC + λ-Carr | Cohesive |
| Alginate + λ-Carr | o-ring failure |
| F127 + CMC + ι-Carr | o-ring failure |

Example 4H: Burst Properties for Viscous Liquid Sealants

The burst test method measured the maximum burst pressure and failure mode of each formulation when applied to samples of harvested porcine pleura. The pleura tissue was freshly harvested and provided before use by Farm to Pharm (Warren, NJ). A 1 mm diameter single defect was created in the mounted tissue sample and purged of air before each application. Each of the viscous sealant groups were expressed in these fixture-wells using the Evicel delivery device attached to a prototype alternating viscous-mixing tip for testing. A syringe pump was used to create the pressure below the tissue surface at an infusion rate of 2 ml/min and was tested until failure. The peak pressure at failure and failure mode was recorded for each sample. The failure modes were defined as cohesive—failure within the sealant, or adhesive—failure at the foam and tissue interface.

Figure 10:
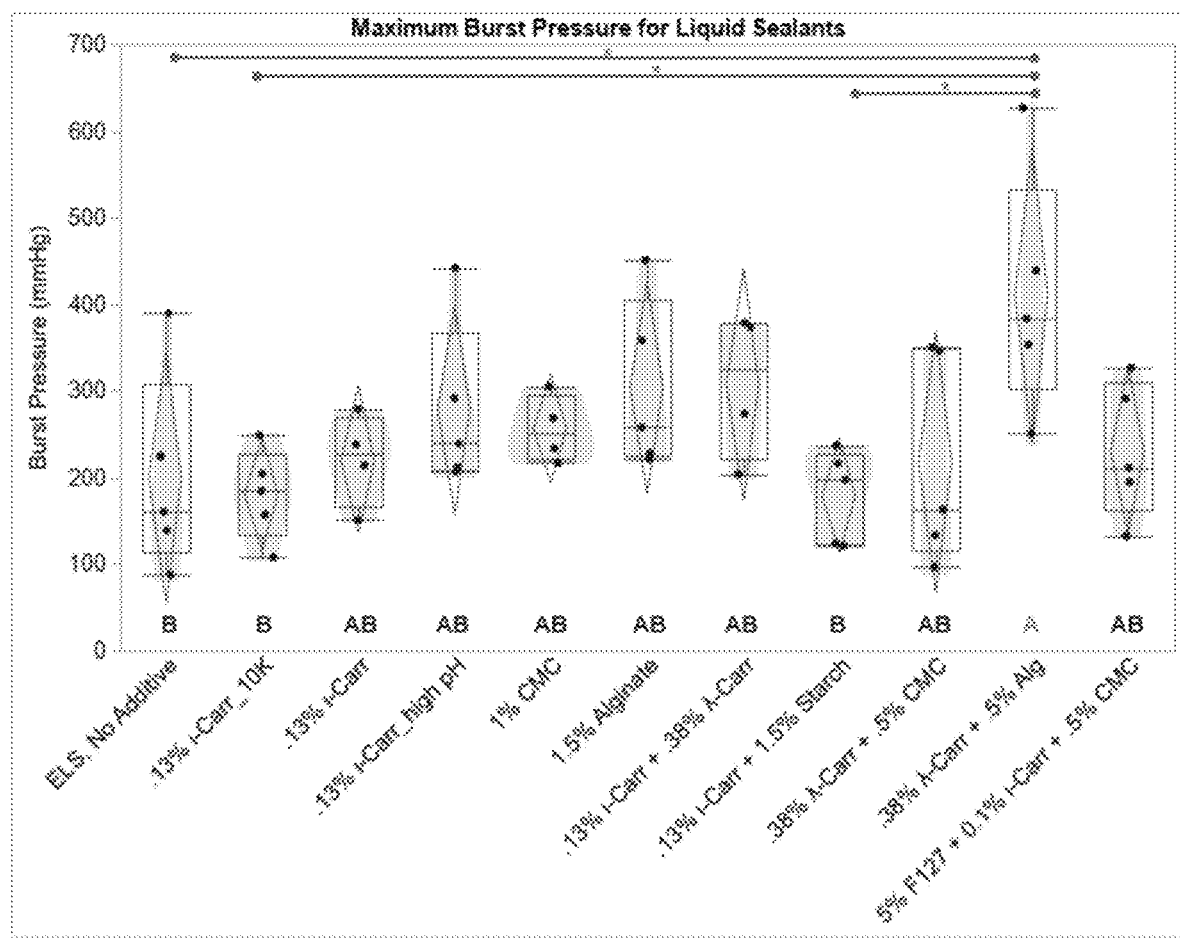

Referring to FIG. 10, a boxplot shows the maximum burst tests The results showed relatively high burst pressures for all formulations. It should be noted that the "5% F127+0.1% ι-Carr+0.5% CMC" solution had lower pH compared to the other formulations. Based the sample size and mean comparisons derived from the Tukey HSD method, all sample formulations with viscosifiers were at least equal to the control. The "Alginate+λ-Carr" sample had a remarkably high mean burst pressure of 410.68 mmHg which was 105% higher than the control. This formulation was also significantly higher in burst pressure when compared to the "ι-Carr, 10K" and "ι-Carr+Starch" formulations. Referring to Table 6 below, the failure modes of tissue adhesion in this burst test, unlike what was seen in the tissue adhesion test above (Table 5), showed mixed cases of adhesive and cohesive failures. Interestingly, the control and the formulations with F127 failed only adhesively whereas the samples with high concentrations of CMC and alginate failed only cohesively.

The sealant formulations described herein demonstrated not only enhanced overall viscosity, enabling retention at application site, but also a benefit to the cohesion of the crosslink network of the sealant. Tensile evaluation demonstrated improvement in elastic strength without needing to compromise on other performance properties of the sealant. Additionally, the hydrogel's linearity in strain that is proportional to the magnitude of applied stress suggests the formulation can easily be tailored to meet the compliance of various bodily tissues, while improving the overall handling properties. As shown and described above, sealant formulations according to the present disclosure, demonstrate high potential for effective performance and applicability utilizing a variety of known biocompatible cross-linking reactants, thereby being both advantageous to the patient and the surgeon.

We claim:

1. A liquid composition for forming a crosslinked sealant for expandable soft tissue comprising:

a reactive hydrogel mixture comprising an electrophilic compound and nucleophilic compound wherein the electrophilic compound includes a multi-arm polyethylene glycol (PEG) based polymer, and wherein the nucleophilic compound includes at least one reactive amine group and the electrophilic compound and nucleophilic compounds are cross-linkable with each other via reaction of the available electrophilic and nucleophilic moieties of each compound;

an amphiphilic poly (akyl) ene glycol block polymer in a range of about 5% to about 15% (w/v) of the sealant composition;

wherein the amphiphilic poly (akyl) ene glycol block polymer is a triblock copolymer consisting of a central block of polypropylene glycol and two end blocks of polyethylene glycol;

and, a buffer solution having a pH in the range of about 8.5 to about 10.5;

wherein the composition has a final crosslinked hydrogel phase having an ultimate extension in the range of about 15 mm to about 40 mm and an ultimate tensile stress in the range of about 2.4 kPa to 5.9 kPa.

2. The liquid composition of claim 1, wherein the buffer solution has a pH in the range of about 8.5 to about 9.0.

3. The liquid composition of claim 1 or claim 2, further comprising a viscosifier.

4. The liquid composition of claim 3, wherein the viscosifier includes at least one of carboxymethyl cellulose (CMC) or carrageenan.

5. The liquid composition of any one of claim 3 or 4, wherein the viscosifier includes a mixture of at least two different viscosifier compounds.

6. The liquid composition of claim 5, wherein the viscosifier is a mixture of carboxymethyl cellulose (CMC) and carrageenan.

7. The liquid composition of any one of claims 3-6, wherein the viscosifier is present in the composition in an amount in the range of about 0.1% to about 10% (w/v).

8. The liquid composition of any one of the preceding claims, wherein the amphiphilic poly (akyl) ene glycol block polymer is in a range of about 7.5% to about 12.5% (w/v) of the sealant composition.

9. The liquid composition of any one of the preceding claims, wherein the electrophilic compound includes a PEG N-hydroxysuccinimide activated ester (PEG-NHS).

10. The liquid composition of claim 8, wherein the PEG-NHS is a PEG-succinimidyl glutarate ester (PEG-SG).

11. The liquid composition of any one of the preceding claims, wherein the nucleophilic compound includes at least one of 4-arm PEG-amine or albumin.

12. A liquid composition for forming a crosslinked sealant for expandable soft tissue consisting essentially of:
 a reactive hydrogel mixture comprising a multi-arm polyethylene glycol (PEG) based polymer having at least one reactive electrophilic group and a multi-arm polymer containing at least one reactive amine group;
 an amphiphilic poly (akyl) ene glycol block polymer in a range of about 5% to about 15% (w/v) of the liquid composition;
 wherein the amphiphilic poly (akyl) ene glycol block polymer is a triblock copolymer consisting of a central block of polypropylene glycol and two end blocks of polyethylene glycol;
 a viscosifier in the range of about 0.1% to about 10% (w/v); and,
 a buffer solution having a pH in the range of about 8.5 to about 9.0;
 and,
 wherein, as measured against a comparative liquid composition having the reactive hydrogel mixture and the buffer solution in the absence of the amphiphilic poly (akyl) ene glycol block polymer, the liquid composition, after cross-linking, has an ultimate extension value and an ultimate stress value greater than an ultimate extension value and an ultimate stress value of comparative liquid composition after cross-linking when measured under the same conditions.

\* \* \* \* \*